United States Patent
Bruce et al.

(10) Patent No.: US 11,291,684 B2
(45) Date of Patent: Apr. 5, 2022

(54) TREATMENT OF GLAUCOMA

(71) Applicant: TX MEDIC AB, Viken (SE)

(72) Inventors: Lars Bruce, Viken (SE); Adam Bruce, Viken (SE)

(73) Assignee: TX MEDIC AB, Viken (SE)

( * ) Notice: Subject to any disclaimer, the term of this patent is extended or adjusted under 35 U.S.C. 154(b) by 220 days.

(21) Appl. No.: 16/614,279

(22) PCT Filed: May 16, 2018

(86) PCT No.: PCT/SE2018/050506
§ 371 (c)(1),
(2) Date: Nov. 15, 2019

(87) PCT Pub. No.: WO2018/212708
PCT Pub. Date: Nov. 22, 2018

(65) Prior Publication Data
US 2021/0315920 A1    Oct. 14, 2021

Related U.S. Application Data

(60) Provisional application No. 62/555,848, filed on Sep. 8, 2017.

(30) Foreign Application Priority Data

May 17, 2017  (SE) .................................... 1750615-5

(51) Int. Cl.
*A61K 31/721*    (2006.01)
*A61P 27/06*    (2006.01)
(Continued)

(52) U.S. Cl.
CPC .......... *A61K 31/721* (2013.01); *A61K 9/0019* (2013.01); *A61K 31/737* (2013.01); *A61P 27/06* (2018.01)

(58) Field of Classification Search
None
See application file for complete search history.

(56) References Cited

U.S. PATENT DOCUMENTS

| 4,238,482 | A | 12/1980 | Peyman et al. |
| 5,135,920 | A | 8/1992 | Kanamaru et al. |

(Continued)

FOREIGN PATENT DOCUMENTS

| CA | 2020199 | A1 | 12/1991 |
| CN | 107137421 | A | 9/2017 |

(Continued)

OTHER PUBLICATIONS

Weinreb et al., "Primary open-angle glaucoma" The Lancet vol. 363 pp. 1711-1720 (Year: 2004).*

(Continued)

*Primary Examiner* — Eric Olson
(74) *Attorney, Agent, or Firm* — Porter Wright Morris & Arthur LLP

(57) ABSTRACT

The present embodiments generally relate to dextran sulfate, or a pharmaceutically acceptable salt thereof, for use in treating, inhibiting or preventing glaucoma in a subject. Dextran sulfate of the embodiments achieves a reduction and normalization of intraocular pressure, a neuroprotective effect in terms of preserving retinal ganglion cells and retinal nerve fiber layer and dissolves established trabecular meshwork scar elements.

27 Claims, 12 Drawing Sheets

(51) Int. Cl.
*A61K 31/737* (2006.01)
*A61K 9/00* (2006.01)

(56) References Cited

U.S. PATENT DOCUMENTS

| | | | |
|---|---|---|---|
| 5,227,372 | A | 7/1993 | Folkman |
| 5,605,938 | A | 2/1997 | Roufa et al. |
| 6,689,764 | B1 | 2/2004 | Shaunak |
| 8,721,622 | B2 | 5/2014 | Agerup |
| 2006/0083711 | A1 | 4/2006 | Berry et al. |
| 2006/0154894 | A1 | 7/2006 | Berry et al. |
| 2013/0273096 | A1 | 10/2013 | Daniels |
| 2014/0186339 | A1 | 7/2014 | Sabbadini et al. |

FOREIGN PATENT DOCUMENTS

| | | |
|---|---|---|
| JP | 2-223525 A | 9/1990 |
| WO | 88/06037 A1 | 8/1988 |
| WO | 99/58126 A1 | 11/1999 |
| WO | 2007/002139 A2 | 1/2007 |
| WO | 2015/175565 A2 | 11/2015 |
| WO | 2015/190989 A1 | 12/2015 |
| WO | 2016/076780 A1 | 5/2016 |
| WO | 2017/018922 A1 | 2/2017 |

OTHER PUBLICATIONS

Almasieh et al., "The molecular basis of retinal ganglion cell death in glaucoma" Progress in Retinal and Eye Research vol. 331 pp. 152-181 doi: 10.1016/j.preteyeres.2011.11.002 (Year: 2012).*

Murgatroyd et al., "Intraocular pressure" COntinuing Education in Anaesthesia, Critical Care, and Pain vol. 8 No. 3 pp. 100-103 doi: 10.1093/bjaceaccp/mkn015 (Year: 2008).*

Bakalash, Sharon et al., Chondroitin Sulfate-Derived Disaccharide Protects Retinal Cells from Elevated Intraocular Pressure in Aged and Immunocompromised Rats, Investigative Ophthalmology & Visual Science, vol. 48, No. 3, pp. 1181-1190 (Mar. 2007).

Shin, Crystal et al., Anti-Angiogenic Polymer Therapeutic for Corneal Neovascularization, Investigative Ophthalmology & Visual Science, vol. 57, No. 3516, pp. 1-2 (Sep. 2016).

Mimura, G. et al., A Clinical Study of Long-Term Administration of Dextran Sulfate (MDS Kowa) in Patients with Retinopathy, Tohoku J. Exp. Med., vol. 141, Suppl., pp. 389-402 (1983).

Ruoslahti, Erkki et al., Effect of Dextran Sulfate on Fibronectin-Collagen Interaction, FEBS Letters, vol. 107, No. 1, pp. 51-54 (1979).

Office Action from corresponding Japanese Application No. 2019-563248 dated Dec. 1, 2020, with English Translation.

* cited by examiner

TREATMENT OF GLAUCOMA

TECHNICAL FIELD

The present embodiments generally relate to prevention, treatment or inhibition of glaucoma, and in particular to the use of dextran sulfate in preventing, treating or inhibiting glaucoma.

BACKGROUND

Glaucoma describes a group of progressive optic neuropathies that have the potential to cause irreversible blindness, in which a main risk factor is raised intraocular pressure (IOP). In primary open-angle glaucoma (POAG), increases in IOP occur when aqueous humor (AqH) outflow through the trabecular meshwork (TM) is reduced, usually as a result of abnormalities in TM cellularity, TM contraction, and extracellular matrix (ECM) levels. The elastic-type fibers in the TM are surrounded by a sheath of fine fibrils embedded in an amorphous ECM made up of collagen IV, laminin, and fibronectin. The presence of plaque material associated with sheaths of the elastic-like fibers in the juxtacanalicular tissue (JCT) within the TM, so-called sheath-derived (SD) plaques, are also a pathological feature of POAG. Thus, POAG patients have significantly more, and thicker, SD-plaques in their TM compared with eyes from age-matched controls. These SD-plaques, however, are not thought to contribute to increased outflow resistance since it has been shown that eyes with psuedoexfoliation glaucoma had similar levels of SD-plaque material when compared with healthy eyes, but still had higher levels of IOP. Nevertheless, increased levels of ECM are seen around TM sheaths and this deposition could contribute to increased outflow resistance. These cellular and ECM changes in the TM, together with altered TM cell contractile abilities result in a dysfunctional TM and ultimately loss of the tight control of AqH outflow.

The mechanisms that lead to TM dysfunction in POAG are probably multifactorial, but pathologically high levels of transforming growth factor-β (TGF-β) within the AqH are thought to contribute. Some POAG patients have elevated levels of TGF-β in their AqH compared with AqH taken from age-matched patients with cataracts or other forms of glaucoma. A role for TGF-β in increasing TM ECM deposition and IOP has been demonstrated by human eye perfusion experiments and in rodent models of glaucoma. Gene expression studies from cultured human TM cells also support the assertion that both TGF-β1 and TGF-β2 isoforms induce the overexpression of ECM proteins that may contribute to TM changes seen in glaucoma. Additionally, TGF-β prevents the breakdown of ECM by inhibiting the activation of matrix metalloproteinases (MMP) through increasing levels of plasminogen activator inhibitor (PAI)-1 and tissue inhibitors of metalloproteinases (TIMP). PAI-1 inhibits the conversion of plasminogen to plasmin, which is required for the plasmin-dependent activation of MMP. The IOP-increasing effects of TGF-β have also been attributed to the ability of the cytokine in reducing proliferation and inducing apoptosis of TM cells, thereby reducing the overall numbers of TM cells.

TGF-β also stimulates contraction of TM cells through the RhoA-Rho-associated protein kinase (ROCK) signaling pathway, with TM contractility significantly influencing IOP. Studies that have reduced or ablated RhoA-mediated TM contraction using Rho/ROCK inhibitors have led to new classes of IOP lowering agents being considered to treat glaucoma and other medical conditions involving increases in IOP. However, it is unlikely that Rho/ROCK inhibitors alone can address the chronic fibrotic pathology that occurs in some patients with POAG, with their efficacy is still under scrutiny. Ultimately, IOP elevations lead to metabolic and biochemical changes in cells of the optic nerve head and retina. Also, mechanical axonal compression affects both retrograde and anterograde axonal transport. The metabolic and biochemical changes together with the mechanical axonal compression deprive retinal ganglion cell (RGC) of neurotrophic factors, which culminates in RGC apoptosis and optic disc cupping, features that are diagnostic of glaucoma.

The goal of any treatment for glaucoma is to prevent loss of vision, as vision loss from glaucoma is irreversible. Currently, glaucoma is treated with eye drops, pills, laser surgery, traditional surgery or a combination of these methods. Most of these treatments are designed to lower and/or control IOP, which can damage the optic nerve that transmits visual information to the brain. However, IOP control is at best imperfect and there is an unmet need for improved therapies that can limit or even reverse disease progression.

SUMMARY

It is a general objective to treat, inhibit or prevent glaucoma in a subject.

This and other objectives are met by embodiments as disclosed herein.

An aspect of the embodiments relates to dextran sulfate, or a pharmaceutically acceptable salt thereof, for use in treating, inhibiting or preventing glaucoma in a subject.

Another aspect of the embodiments relates to dextran sulfate, or a pharmaceutically acceptable salt thereof, for use in treating, inhibiting or preventing ocular hypertension in a subject.

A further aspect of the embodiments relates to dextran sulfate, or a pharmaceutically acceptable salt thereof, for use in inhibiting loss of retinal ganglion cells and reduction of retinal nerve fiber layer in a subject suffering from glaucoma and/or ocular hypertension.

Yet another aspect of the embodiments relates to dextran sulfate, or a pharmaceutically acceptable salt thereof, for use in reducing intraocular pressure in a subject suffering from glaucoma.

Further aspects of the embodiments relates to use of dextran sulfate, or a pharmaceutically acceptable salt thereof, for the manufacture of a medicament for treatment, inhibition or prevention of glaucoma in a subject; for treatment, inhibition or prevention of ocular hypertension in a subject; for reducing intraocular pressure in a subject suffering from glaucoma; or for loss of retinal ganglion cells and reduction of retinal nerve fiber layer in a subject suffering from glaucoma and/or ocular hypertension.

Yet another aspect of the embodiments relates to a method of treating, inhibiting or preventing glaucoma. The method comprises administering dextran sulfate, or a pharmaceutically acceptable derivative thereof, to a subject suffering from glaucoma.

A further aspect of the embodiments relates to a method of treating, inhibiting or preventing ocular hypertension. The method comprises administering dextran sulfate, or a pharmaceutically acceptable derivative thereof, to a subject suffering from ocular hypertension.

Another aspect of the embodiments relates to a method of inhibiting loss of retinal ganglion cells and reduction of retinal nerve fiber layer. The method comprises administering dextran sulfate, or a pharmaceutically acceptable derivative thereof, to a subject suffering from glaucoma and/or ocular hypertension.

Yet another aspect of the embodiments relates to a method of reducing intraocular pressure in a subject suffering from glaucoma. The method comprises administering dextran sulfate, or a pharmaceutically acceptable derivative thereof, to the subject suffering from glaucoma.

Dextran sulfate of the present embodiments causes a rapid and reproducible restoration of normal IOP in subjects suffering from glaucoma. The reduction in IOP down to the normal range of healthy subjects was associated with preservation of RGCs in the retina and a preservation of the retinal nerve fiber layer (RNFL). The restoration of normal IOP levels is suggested to result from dissolution of established TM scar elements as verified by significantly reduced levels of laminin and fibronectin in the angle of subjects treated by dextran sulfate.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1:
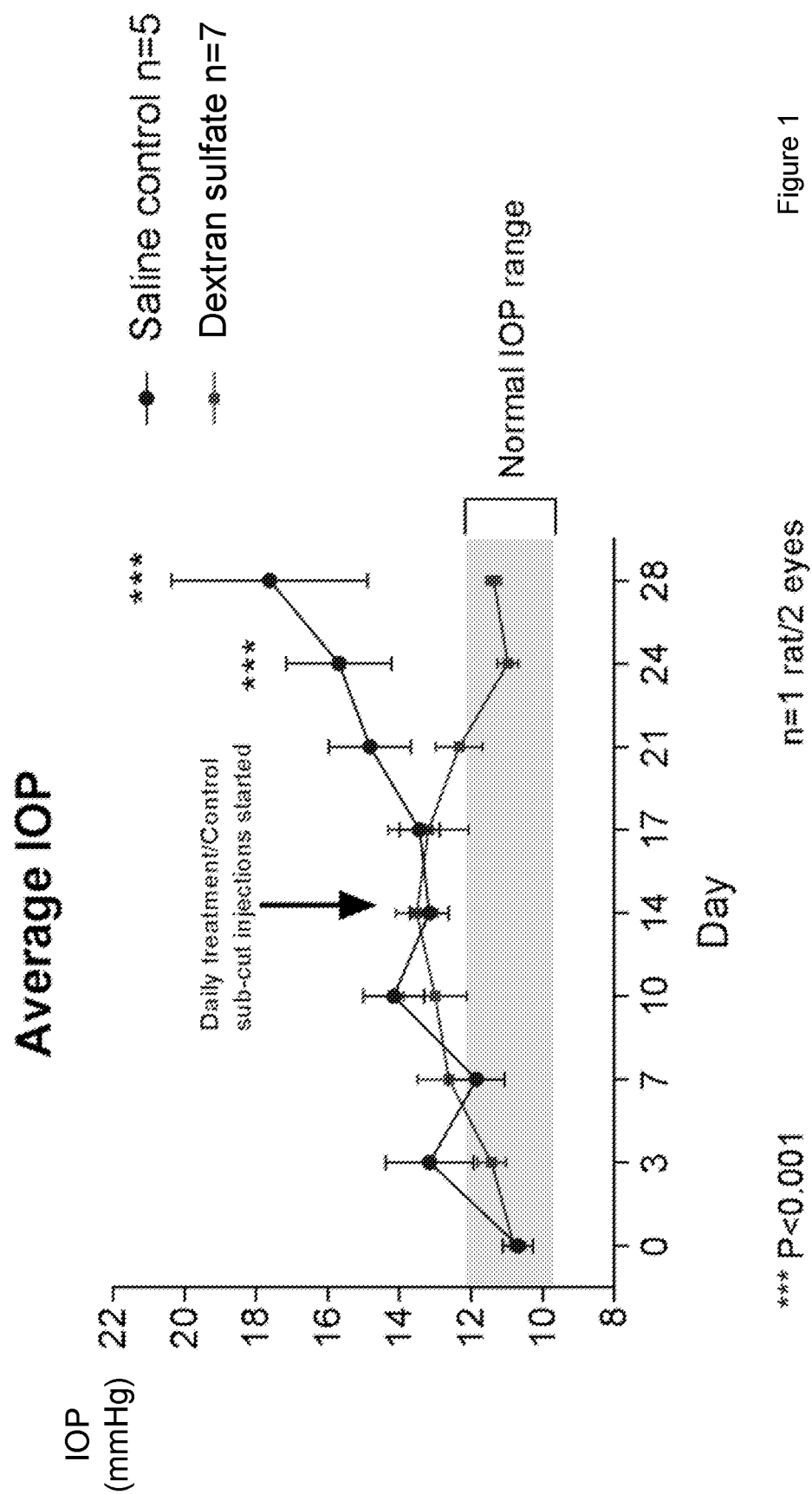
FIG. 1 illustrates changes in intraocular pressure (IOP) in subjects suffering from primary open-angle glaucoma (POAG) and treated with saline control or dextran sulfate according to the embodiments.

The present embodiments generally relate to prevention, treatment or inhibition of glaucoma, and in particular to the use of dextran sulfate in preventing, treating or inhibiting glaucoma.

Dextran sulfate treatment led to a rapid and reproducible restoration of normal intraocular pressure (IOP) in glaucomatous eyes in subjects suffering from glaucoma, and in particular primary open-angle glaucoma (POAG). Restoration of normal IOP levels was associated with preservation of retinal ganglion cell (RGC) in the retina as evidenced by maintained RGC counts and a preservation of retinal nerve fiber layer (RNFL) thickness in eyes from dextran sulfate treated subjects. Dextran sulfate treatment also resulted in dissolution of established trabecular meshwork (TM) scar elements as levels of laminin and fibronectin were significantly lower in the angle of dextran sulfate treated subjects.

The clinical implications of the observations are as follows. Patients with glaucoma are currently treated by daily eye drops of drugs that lower IOP either by limiting ocular fluid production or increasing ocular fluid outflow. These treatments have poor compliance and, consequently, IOP is imperfectly controlled, leading to progressive vision loss in most patients. A treatment that prevents and reverses the ocular pathology leading to vision loss and significantly improves IOP control would be highly valuable.

Candidate drugs useful in treating glaucoma should not induce angiogenesis or neovascularization in the eyes. Such pathologic angiogenesis in the eye may otherwise lead to severe visual impairment. Experimental data as presented herein indicates that dextran sulfate did not have antiangiogenic or pro-angiogenic effects on the eyes of treated subjects. Accordingly, dextran sulfate can therefore safely be used in ocular indications without the risk of pathologic angiogenesis in the eye.

Dextran sulfate of the embodiments can thereby effectively be used in prevention, treatment of inhibition of glaucoma.

Accordingly, an aspect of the embodiments relates to dextran sulfate, or a pharmaceutically acceptable salt thereof, for use in treating, inhibiting or preventing glaucoma in a subject.

Glaucoma is a group of eye diseases, which result in damage to the optic nerve and retina with associated vision loss. The most common type of glaucoma is open-angle glaucoma with less common types including closed-angle glaucoma and normal-tension glaucoma. Open-angle glaucoma develops slowly over time and there is no pain. Side vision may begin to decrease followed by central vision loss resulting in blindness if not treated. Closed-angle glaucoma can present gradually or suddenly. The sudden presentation may involve severe eye pain, blurred vision, mid-dilated pupil, redness of the eye, and nausea. Vision loss from glaucoma, once it has occurred, is permanent.

If treated early it may be possible to slow or stop the progression of the glaucoma disease with medication, laser treatment, or surgery. The modern goals of glaucoma management are to avoid glaucomatous damage and nerve damage, and preserve visual field and total quality of life for patients, with minimal side effects. This requires appropriate diagnostic techniques and follow-up examinations, and judicious selection of treatments for the individual patient. Although intraocular pressure is only one of the major risk factors for glaucoma, lowering it via various pharmaceuticals and/or surgical techniques is currently the mainstay of glaucoma treatment.

Intraocular pressure can be lowered with medication, usually eye drops. Several classes of medications are used to treat glaucoma, with several medications in each class. Each of these medicines may have local and systemic side effects. Adherence to medication protocol can be confusing and expensive. Poor compliance with medications and follow-up visits is a major reason for vision loss in glaucoma patients.

Both laser and conventional surgeries are performed to treat glaucoma. Surgery and laser treatment are generally temporary solutions, as they are not able to cure glaucoma.

Thus, there is a long felt need to provide a medicament that can be used to treat, inhibit or prevent glaucoma in a subject.

Dextran sulfate, or a pharmaceutically acceptable salt, according to the embodiments induces, when administered to a subject suffering from increased IOP, i.e., ocular hypertension, such as caused by glaucoma, a reduction of the IOP. In fact, the IOP is normalized, i.e., reduced to normal IOP range of healthy subjects, following dextran sulfate administration. Accordingly, dextran sulfate, or the pharmaceutically acceptable salt thereof, according to the embodiments is able to combat and treat one of the most deleterious components of glaucoma, i.e., the abnormal and increased IOP.

Furthermore, administration of dextran sulfate, or the pharmaceutically acceptable salt thereof, according to the embodiments provides a neuroprotective effect to the RGCs. In more detail, dextran sulfate administration protected the RGCs from damage and cell death as seen in maintained RGC counts and a preservation of RNFL thickness in the eyes of the treated subjects.

RGC is a type of neuron located near the inner surface of the retina of the eye, typically denoted ganglion cell layer. RGCs collectively transmit image-forming and non-image forming visual information from the retina in the form of action potential to several regions in the thalamus, hypothalamus, and mesencephalon, or midbrain. RGCs vary significantly in terms of their size, connections, and responses to visual stimulation but they all share the defining property of having a long axon that extends into the brain. These axons form the optic nerve, optic chiasm, and optic tract.

The RNFL, sometimes denoted nerve fiber layer or stratum opticum, is formed by the expansion of the fibers of the optic nerve. The RNFL is a sensitive structure and some processes, such as high IOP, can excite its natural apoptosis.

The neuroprotective effect of dextran sulfate, or the pharmaceutically acceptable salt thereof, of the embodiments effectively prevents damage and apoptosis of the RGCs and thereby a preservation of the RNFL.

As mentioned in the foregoing, TM dysfunction, such as abnormalities in TM cellularity and TM contraction, may be an underlying cause of high IOP as seen in subjects suffering from glaucoma. Dextran sulfate, or the pharmaceutically acceptable salt thereof, of the embodiments disperses and attenuates TM scarring established in glaucoma subjects. This, in turn, normalizes AqH outflow through the TM.

The anti-scarring effect of dextran sulfate, or the pharmaceutically acceptable salt thereof, of the embodiments is suggested to be the result of several mechanisms induced by dextran sulfate, or the pharmaceutically acceptable salt thereof. Thus, dextran sulfate, or the pharmaceutically acceptable salt thereof, induces matrix metalloproteinases (MMP), which are enzymes capable of degrading extracellular matrix (ECM) proteins and suppress the activity of tissue inhibitors of metalloproteinases (TIMPs).

Dextran sulfate, or the pharmaceutically acceptable salt thereof, further induces natural anti-scarring molecules, such as decorin, which in turn blocks TGF-β and various growth factors, such as hepatocyte growth factor (HGF), insulin-like growth factor (IGF), vascular endothelial growth factor (VEGF), tumor necrosis factor (TNF), etc. Dextran sulfate, or the pharmaceutically acceptable salt thereof, also has inhibitory effect on TGF-β activity and inhibits fibrosis even in the presence of excessive levels of TGF-β. Dextran sulfate, or the pharmaceutically acceptable salt thereof, further inhibits immune cell adhesion and cell aggregation. Scarring is driven by inflammatory cytokines, in particular TGF-β, and suppresses levels of TGF-β-activated protein kinase 1 (TAK-1). Dextran sulfate, or the pharmaceutically acceptable salt thereof, blocks TGF-β and other cytokines that promote scarring and fibrosis and is in parallel stimulating anti-scarring molecules. Taken together these mechanisms induced by dextran sulfate, or the pharmaceutically acceptable salt thereof, have positive effect in glaucomatous eyes by dispersing and attenuating TM scarring.

Prior art anti-glaucoma medicaments are generally not capable of treating or curing glaucoma nor combating the underlying causes of glaucoma but rather alleviates symptoms of glaucoma, such as lower IOP either by limiting ocular fluid production or increasing ocular fluid outflow. However, treatments using such medicaments typically have poor compliance and imperfect IOP control, thereby leading to progressive vision loss in most subjects. This is in clear contrast to dextran sulfate, or the pharmaceutically acceptable salt thereof, of the embodiments that not only reduces and normalizes IOP but also provides a neuroprotective effect on RGCs and the RNFL and dissolves the established TM scar elements to thereby enable an actual inhibition and treatment of glaucoma.

Dextran sulfate, or the pharmaceutically acceptable salt thereof, achieves the treatment, inhibition or prevention of glaucoma without causing pathologic angiogenesis in the eye. Thus, it is important that a medicament used for glaucoma treatment, inhibition or prevention do not induce angiogenesis or neovascularization in the eyes, which otherwise would lead to severe visual impairment. Experimental data as presented herein indicates that dextran sulfate, or the pharmaceutically acceptable salt thereof, had neither anti-angiogenic nor pro-angiogenic effects in the eye and is thereby suitable for application in ocular indications.

Open-angle glaucoma is the most common form of glaucoma, accounting for at least 90% of all glaucoma cases. It is caused by the clogging of the drainage canals, resulting in increased eye pressure. Open-angle means that the angle where the iris meets the cornea is as wide and open as it should be. Open-angle glaucoma is also referred to as primary glaucoma, primary open-angle glaucoma (POAG), or chronic glaucoma in the art.

In a particular embodiment, dextran sulfate, or the pharmaceutically acceptable salt thereof, is for use in treating, inhibiting or preventing open-angle glaucoma, such as POAG, in a subject.

Dextran sulfate, or the pharmaceutically acceptable salt thereof, effectively reduces IOP from ocular hypertension ranges back to normal IOP range.

Thus, another aspect of the embodiments relates to dextran sulfate, or a pharmaceutically acceptable salt thereof, for use in treating, inhibiting or preventing ocular hypertension in a subject.

In a particular embodiment, dextran sulfate, or the pharmaceutically acceptable salt thereof, is for use in reducing intraocular pressure in a subject suffering from ocular hypertension.

Hence, an aspect of the embodiments relates to dextran sulfate, or a pharmaceutically acceptable salt thereof, for use in reducing intraocular pressure in a subject suffering from glaucoma, preferably suffering from open-angle glaucoma, such as POAG.

In humans, normal IOP range is typically between 10 mmHg and 20 mmHg, with the average value of IOP about 15.5 mmHg with fluctuations of about 2.75 mmHg. Ocular hypertension (OHT) is defined as an IOP being higher than normal, i.e., typically higher than 20 mmHg for humans.

Thus, in an embodiment, reducing intraocular pressure comprises reducing intraocular pressure, or restoring intraocular pressure, to be within a normal IOP range from 10 mmHg up to 20 mmHg, such as within an IOP range from 12.75 mmHg up to 18.25 mmHg.

In an embodiment, the subject is suffering from ocular hypertension caused by glaucoma, preferably open-angle glaucoma, such as POAG.

Although glaucoma, and in particular open-angle glaucoma and POAG, is a main cause of ocular hypertension, there are other possible causes of ocular hypertension including, for instance, high blood pressure; stress; a diet with excess salt, hydrogenated oils, alcohol and sugar; eye trauma; smoking; diabetes; and heart disease. Also some medicaments have the side effect of causing ocular hypertension in certain individuals. For instance, steroid medicines used to treat asthma and other conditions have been shown to increase the risk of ocular hypertension. Various eye traumas that may affect the balance of aqueous production and drainage from the eye can cause ocular hypertension. Ocular hypertension has also been associated with other eye conditions, such as nocturnal raised IOP, IOP spiking, pseudoexfoliation syndrome, pigment dispersion syndrome and corneal arcus.

Dextran sulfate, or the pharmaceutically acceptable salt thereof, provides a neuroprotective effect to prevent or at least reduce damages and death to RGCs and preserve RNFL integrity and thickness.

Thus, a further aspect of the embodiments relates to dextran sulfate, or a pharmaceutically acceptable salt thereof, for use in inhibiting loss of retinal ganglion cells and reduction of retinal nerve fiber layer in a subject suffering from glaucoma, preferably open-angle glaucoma, such as POAG, and/or ocular hypertension.

The increased IOP and death of RGCs may also, directly or indirectly, affect other retinal neurons, such as interneurons and photoreceptors. For instance, death of RGC may cause atrophy, which in turn induced loss of synapses and death of other retinal neurons.

Accordingly, normalizing IOP and reducing damages and death of RGCs will be useful in treating, preventing or inhibiting other retinal conditions, such as diabetic retinopathy and various genetic conditions linked to loss of photoreceptors.

Dextran sulfate, or the pharmaceutically acceptable salt thereof, is a unique agent for the treatment, prevention or inhibition of glaucoma and related retinal conditions by not only lowering IOP but also simultaneously directly protecting retinal neurons from damage and death.

In an embodiment, dextran sulfate, or the pharmaceutically acceptable salt thereof, is formulated for systemic administration to the subject. In an embodiment, dextran sulfate, or the pharmaceutically acceptable salt thereof, is formulated for parenteral administration as an example of systemic administration.

Examples of parenteral administration routes include intravenous (i.v.) administration, intra-arterial administration, intra-muscular administration, intracerebral administration, intracerebroventricular administration, intrathecal administration and subcutaneous (s.c.) administration.

In an embodiment, dextran sulfate, or the pharmaceutically acceptable salt thereof, is preferably formulated for intravenous (i.v.) or subcutaneous (s.c.) administration to the subject. Accordingly, i.v. and s.c. administration are preferred examples of systemic administration of dextran sulfate, or the pharmaceutically acceptable salt thereof. In a particular embodiment, dextran sulfate, or the pharmaceutically acceptable salt thereof, is formulated for s.c. administration to the subject.

In an embodiment, dextran sulfate, or the pharmaceutically acceptable salt thereof, is formulated as an aqueous injection solution, preferably as an aqueous i.v. or s.c. injection solution. Thus, dextran sulfate, or the pharmaceutically acceptable salt thereof, of the embodiments is preferably formulated as an aqueous injection solution with a selected solvent or excipient. The solvent is advantageously an aqueous solvent and in particular a buffer solution. A non-limiting example of such a buffer solution is a citric acid buffer, such as citric acid monohydrate (CAM) buffer, or a phosphate buffer. For instance, dextran sulfate of the embodiments can be dissolved in saline, such as 0.9% NaCl saline, and then optionally buffered with 75 mM CAM and adjusting the pH to about 5.9 using sodium hydroxide. Also non-buffered solutions are possible, including aqueous injection solutions, such as saline, i.e., NaCl (aq). Furthermore, other buffer systems than CAM and phosphate buffers could be used if a buffered solution is desired.

The embodiments are not limited to injections and other administration routes can alternatively be used including intraocular, intravitreal, transzonular, nasal, buccal, dermal, tracheal, bronchial, or topical administration. The active compound, dextran sulfate, is then formulated with a suitable excipient, solvent or carrier that is selected based on the particular administration route.

Intraocular administration refers to an administration entering the eyeball of a subject. Intravitreal administration refers to an administration through an eye of a subject, preferably directly into the inner cavity of the eye. Transzonular administration refers to an administration through the ciliary zonule, which is a series of fibers connecting the ciliary body and the lens of the eye.

Carrier refers to a substance that serves as a vehicle for improving the efficiency of delivery and/or the effectiveness of dextran sulfate, or the pharmaceutically acceptable salt thereof.

Excipient refers to a pharmacologically inactive substance that is formulated in combination with dextran sulfate, or the pharmaceutically acceptable salt thereof, and includes, for instance, bulking agents, fillers, diluents and products used for facilitating drug absorption or solubility or for other pharmacokinetic considerations.

Pharmaceutically acceptable salt of dextran sulfate refers to a salt of dextran sulfate having the effects as disclosed herein and not being deleterious to the recipient thereof at the administered dose(s).

Dextran sulfate is preferably a so-called low molecular weight dextran sulfate.

In the following, reference to (average) molecular weight and sulfur content of dextran sulfate applies also to any pharmaceutically acceptable salt of dextran sulfate. Hence, the pharmaceutically acceptable salt of dextran sulfate preferably has the average molecular weight and sulfur content as discussed in the following embodiments.

Dextran sulfate is a sulfated polysaccharide and in particular a sulfated glucan, i.e., a polysaccharide made of many glucose molecules. Average molecular weight as defined herein indicates that individual sulfated polysaccharides may have a molecular weight different from this average molecular weight but that the average molecular weight represents the mean molecular weight of the sulfated polysaccharides. This further implies that there will be a natural distribution of molecular weights around this average molecular weight for a dextran sulfate sample.

Average molecular weight ($M_w$) of dextran sulfate is typically determined using indirect methods, such as gel exclusion/penetration chromatography, light scattering or viscosity. Determination of average molecular weight using such indirect methods will depend on a number of factors, including choice of column and eluent, flow rate, calibration procedures, etc.

Average molecular weight ($M_w$):

$$\frac{\Sigma M_i^2 N_i}{\Sigma M_i N_i},$$

typical tor methods sensitive to molecular size rather than numerical value, e.g., light scattering and size exclusion chromatography (SEC) methods. If a normal distribution is assumed, then a same weight on each side of $M_w$, i.e., the total weight of dextran sulfate molecules in the sample having a molecular weight below $M_w$ is equal to the total weight of dextran sulfate molecules in the sample having a molecular weight above $M_w$.

In an embodiment, dextran sulfate, or the pharmaceutically acceptable salt thereof, preferably has an average molecular weight equal to or below 40000 Da, more preferably equal to or below 20000 Da and in particular equal to or below 10000 Da.

Dextran sulfate of an average molecular weight exceeding 10000 Da generally has a lower effect vs. toxicity profile as compared to dextran sulfate having a lower average molecular weight. This means that the maximum dose of dextran sulfate that can be safely administered to a subject is lower for larger dextran sulfate molecules (>10000 Da) as compared to dextran sulfate molecules having an average molecular weight within the preferred range. As a consequence, such larger dextran sulfate molecules are less appropriate in clinical uses when the dextran sulfate is to be administered to subjects in vivo.

In an embodiment, dextran sulfate, or the pharmaceutically acceptable salt thereof, has an average molecular weight within a range of 2000 and 10000 Da. In another embodiment, the average molecular weight is within a range of 2500 and 10000 Da. In a particular preferred embodiment, the average molecular weight is within a range of 3000 to 10000 Da.

In an optional, but preferred embodiment, less than 40% of the dextran sulfate molecules have a molecular weight below 3000 Da, preferably less than 35%, such as less than 30% or less than 25% of the dextran sulfate molecules have a molecular weight below 3000 Da. In addition, or alternatively, less than 20% of the dextran sulfate molecules have a molecular weight above 10000 Da, preferably less than 15%, such as less than 10% or less than 5% of the dextran sulfate molecules have a molecular weight above 10000 Da. Thus, in a particular embodiment, the dextran sulfate has a substantially narrow molecular weight distribution around the average molecular weight.

In a particular embodiment, the average molecular weight of dextran sulfate, or the pharmaceutically acceptable salt thereof, is within a range of 3500 and 9500 Da, such as within a range of 3500 and 8000 Da.

In another particular embodiment, the average molecular weight of dextran sulfate, or the pharmaceutically acceptable salt thereof, is within a range of 4500 and 7500 Da.

In a further particular embodiment, the average molecular weight of dextran sulfate, or the pharmaceutically acceptable salt thereof, is within a range of 4500 and 5500 Da.

Thus, in a currently preferred embodiment the average molecular weight of dextran sulfate, or the pharmaceutically acceptable salt thereof, is preferably approximately 5000 Da or at least substantially close to 5000 Da, such as 5000±500 Da, for instance 5000±400 Da, preferably 5000±300 Da or 5000±200 Da, such as 5000±100 Da. Hence, in an embodiment, the average molecular weight of dextran sulfate, or the pharmaceutically acceptable salt thereof, is 4.5 kDa, 4.6 kDa, 4.7 kDa, 4.8 kDa, 4.9 kDa, 5.0 kDa, 5.1 kDa, 5.2 kDa, 5.3 kDa, 5.4 kDa or 5.5 kDa.

In a particular embodiment, the average molecular weight of dextran sulfate, or the pharmaceutically salt thereof as presented above is average $M_w$, and preferably determined by gel exclusion/penetration chromatography, size exclusion chromatography, light scattering or viscosity-based methods.

In a particular embodiment, dextran sulfate, or the pharmaceutically acceptable salt thereof, consists, on average, of about or slightly above 5 glucose units and has an average sulfate number per glucose unit of at least 2.0, such as of at least 2.5.

Dextran sulfate is a polyanionic derivate of dextran and contains sulfur. The average sulfur content for dextran sulfate of the embodiments is preferably 15 to 20% and more preferably approximately 17%, generally corresponding to about or at least two sulfate groups per glucosyl residue. In a particular embodiment, the sulfur content of dextran sulfate is preferably equal to or at least close to the maximum possible degree of sulfur content of the corresponding dextran molecules.

In a particular embodiment, dextran sulfate of the embodiments has a number average molecular weight ($M_n$) as measured by nuclear magnetic resonance (NMR) spectroscopy within an interval of 1850 and 3500 Da.

Number average molecular weight ($M_n$):

$$\frac{\Sigma M_i N_i}{\Sigma N_i},$$

typically derived by end group assays, e.g., NMR spectroscopy or chromatography. If a normal distribution is assumed, then a same number of dextran sulfate molecules can be found on each side of $M_n$, i.e., the number of dextran sulfate molecules in the sample having a molecular weight below $M_n$ is equal to the number of dextran sulfate molecules in the sample having a molecular weight above $M_n$.

In a preferred embodiment, dextran sulfate of the embodiments has a $M_n$ as measured by NMR spectroscopy within an interval of 1850 and 2500 Da, preferably within an interval of 1850 and 2300 Da, and more preferably within an interval of 1850 and 2000 Da.

In a particular embodiment, dextran sulfate of the embodiments has an average sulfate number per glucose unit within an interval of 2.5 and 3.0, preferably within an interval of 2.5 and 2.8, and more preferably within an interval of 2.6 and 2.7.

In a particular embodiment, dextran sulfate of the embodiments has an average number of glucose units within an interval of 4.0 and 6.0, preferably within an interval of 4.5 and 5.5, and more preferably within an interval of 5.0 and 5.2, such as about 5.1.

In another particular embodiment, dextran sulfate of the embodiments has on average 5.1 glucose units and an average sulfate number per glucose unit of 2.6 to 2.7, typically resulting in a number average molecular weight ($M_n$) as measured by NMR spectroscopy within an interval of 1850 and 2000 Da.

A dextran sulfate, or pharmaceutically salt thereof, that can be used according to the embodiments is described in WO 2016/076780.

The dextran sulfate according to the embodiments can be provided as a pharmaceutically acceptable salt of dextran sulfate. Such pharmaceutically acceptable salts include e.g., a sodium or potassium salt of dextran sulfate.

In a particular embodiment, the sodium salt of dextran sulfate, including $Na^+$ counter ions, has a $M_n$ as measured by NMR spectroscopy within an interval of 2000 and 2500 Da, preferably within an interval of 2100 and 2300 Da.

Suitable dose ranges for the dextran sulfate, or the pharmaceutically acceptable salt thereof, of the embodiments may vary according to the size and weight of the subject, the condition for which the subject is treated, and other considerations. In particular for human subjects, a possible dosage range could be from 1 μg/kg to 150 mg/kg of body weight, preferably from 10 μg/kg to 100 mg/kg of body weight.

In preferred embodiments, dextran sulfate, or the pharmaceutically acceptable salt thereof, is formulated to be administered at a dosage in a range from 0.05 to 50 mg/kg of body weight of the subject, preferably from 0.05 or 0.1 to 40 mg/kg of body weight of the subject, and more preferably from 0.05 or 0.1 to 30 mg/kg, or 0.1 to 25 mg/kg or from 0.1 to 15 mg/kg or 0.1 to 10 mg/kg body weight of the subject.

Administration of dextran sulfate, or the pharmaceutically acceptable salt thereof, of the embodiments is preferably initiated as soon as possible after occurrence of an event or condition that may otherwise cause glaucoma, ocular hypertension and/or damages to RGCs and the RNFL in the subject.

Administration of dextran sulfate, or the pharmaceutically acceptable salt thereof, does not necessarily have to be limited to treatment of glaucoma but could alternatively, or in addition, be used for prophylaxis. In other words, dextran sulfate of the embodiments could be administered to a subject having an increased risk of developing glaucoma, ocular hypertension and/or damages to RGCs and the RNFL.

Inhibition of glaucoma, of ocular hypertension and/or of loss of RGCs and of reduction of the RNFL as used herein implies that dextran sulfate, or the pharmaceutically acceptable salt thereof, reduces the symptoms and effects of the condition even though a 100% treatment or cure does not necessarily occur. For instance, inhibition of ocular hypertension involves a reduction in the IOP, possibly even down to normal IOP range, such as equal to or below 20 mmHg. Inhibition of loss of RGCs involves reducing the number of RGC that may otherwise be damaged or lost, including up to preventing any RGC loss above any normal RGC loss seen in healthy subjects. Correspondingly, inhibition of reduction of RNFL involves stopping or at least decreasing any reduction in RNFL thickness, including up to preventing any RNFL reduction above any normal RNFL reduction seen in healthy subjects. Inhibition of glaucoma includes reducing or at least mitigating symptoms and conditions caused by glaucoma, such as reducing IOP, reducing RGC loss, decreasing RNFL reduction and/or dissolving TM scar elements.

Dextran sulfate, or the pharmaceutically acceptable salt thereof, of the embodiments can be administered at a single administration occasion, such as in the form of a single injection or bolus injection. This bolus dose can be injected quite quickly to the patient but is advantageously infused over time so that the dextran sulfate solution is infused over a few minutes of time to the patient, such as during 5 to 10 minutes or more.

Alternatively, dextran sulfate, or the pharmaceutically acceptable salt thereof, of the embodiments can be administered at multiple, i.e., at least two, occasions during a treatment period. Thus, dextran sulfate of the embodiments could be administered once or at multiple times per day, once or at multiple times per week, once or at multiple times per month as illustrative examples.

In a particular embodiment, dextran sulfate, or the pharmaceutically acceptable salt thereof, is formulated for administration at multiple times, such as 2-14 times, preferably 2-7 times, a week for one or multiple consecutive weeks, such as at least 2-5 consecutive weeks. In a particular embodiment, dextran sulfate, or the pharmaceutically acceptable salt thereof, is formulated for administration once or twice a day for multiple days, such as multiple consecutive days, e.g., 2-14 days.

In an embodiment, the subject is a mammalian subject, preferably a primate, and more preferably a human subject. Although the embodiments are in particular directed towards treating, inhibiting or preventing glaucoma in human subjects, the embodiments may also, or alternatively, be used in veterinary applications. Non-limiting example of animal subjects include primate, cat, dog, pig, horse, mouse, rat.

Other aspects of the embodiments relates to use of dextran sulfate, or a pharmaceutically acceptable salt thereof, for the manufacture of a medicament for treatment, inhibition or prevention of glaucoma in a subject; for treatment, inhibition or prevention of ocular hypertension in a subject; for reducing intraocular pressure in a subject suffering from glaucoma; or for loss of RGCs and reduction of RNFL in a subject suffering from glaucoma, preferably open-angle glaucoma, and/or ocular hypertension.

Yet another aspect of the embodiments relates to a method of treating, inhibiting or preventing glaucoma. The method comprises administering dextran sulfate, or a pharmaceutically acceptable derivative thereof, to a subject suffering from glaucoma, preferably open-angle glaucoma.

A further aspect of the embodiments relates to a method of treating, inhibiting or preventing ocular hypertension. The method comprises administering dextran sulfate, or a pharmaceutically acceptable derivative thereof, to a subject suffering from ocular hypertension.

Another aspect of the embodiments relates to a method of inhibiting loss of retinal ganglion cells and reduction of retinal nerve fiber layer. The method comprises administering dextran sulfate, or a pharmaceutically acceptable derivative thereof, to a subject suffering from glaucoma, preferably open-angle glaucoma, and/or ocular hypertension.

Yet another aspect of the embodiments relates to a method of reducing intraocular pressure in a subject suffering from glaucoma. The method comprises administering dextran sulfate, or a pharmaceutically acceptable derivative thereof, to the subject suffering from glaucoma.

EXAMPLES

Example 1—Effect of Dextran Sulfate on Glaucomatous Eyes

Results

Intraocular Pressure (IOP)

Raised IOP was induced by twice weekly intracameral injections of the inflammatory cytokine TGF-β over the entire time period of 28 days. This induced scarring of the trabecular meshwork (TM) drainage portals by day 14 with associated raised IOP. Daily subcutaneous dextran sulfate/saline treatments commenced at day 14.

IOP was raised at day 14 in both groups, with raised IOP progressing in animals receiving subcutaneous saline injections. However, the elevated IOP started to reduce after 7 days of dextran sulfate treatment and by day 24 there was a significantly lower ($P<0.001$) and normalized IOP in the dextran sulfate group compared to controls. The IOP remained significantly lower ($P>0.001$) than the control group at the end of the experiment on day 28 (FIG. 1).

Retinal Ganglion Cell (RGC) Numbers

Figure 2:
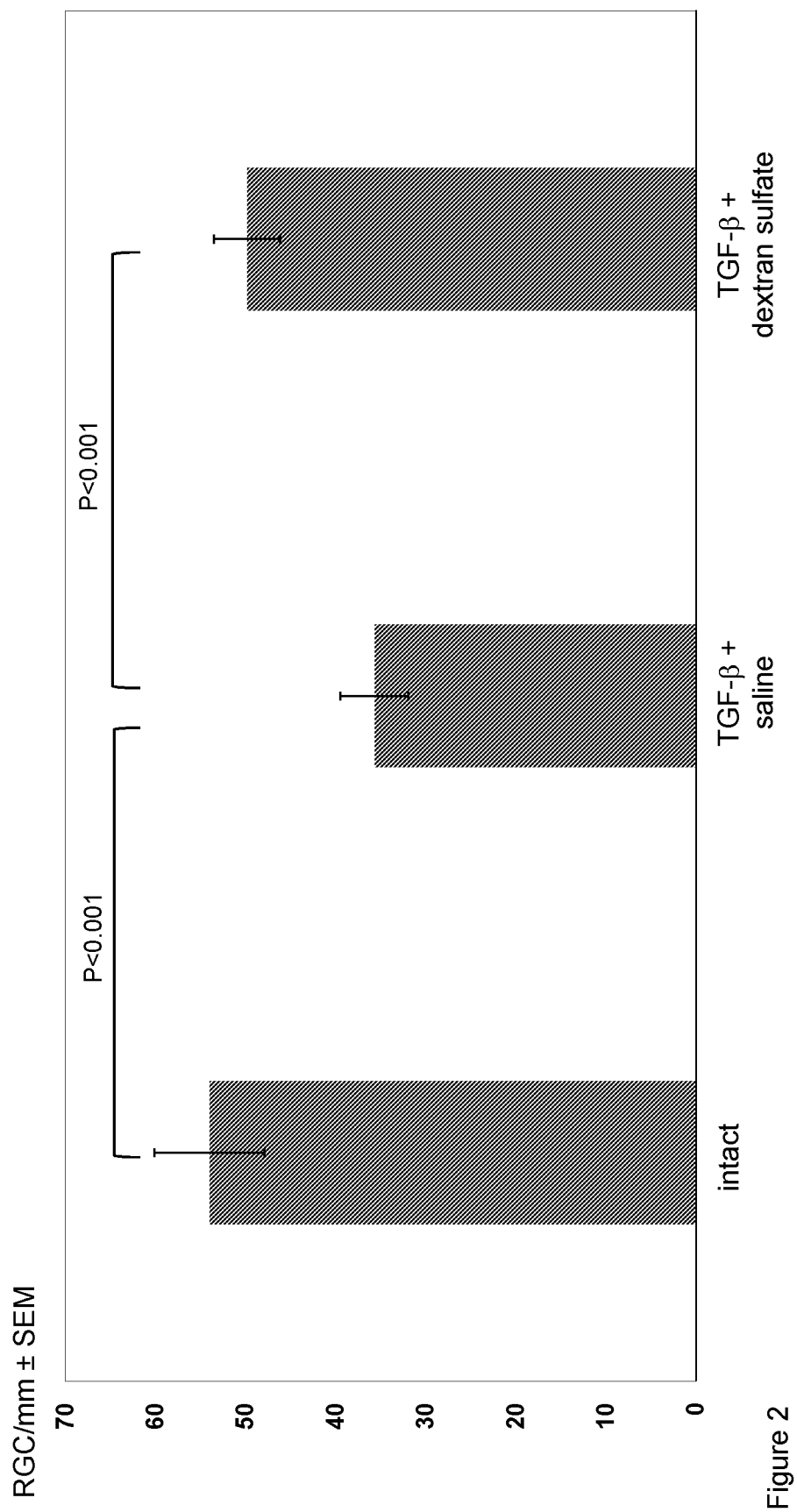
FIG. 2 illustrates changes in retinal ganglion cell (RGC) number in subjects suffering from POAG and treated with saline control or dextran sulfate according to the embodiments.

Dextran sulfate treatment significantly prevented ($P>0.001$) the decline in RGC numbers present in the retina at day 28 (FIG. 2), suggesting a neuroprotective effect of dextran sulfate. This neuroprotective effect may be via a direct or indirect effect due to the lowered IOP.

Optical Coherence Tomography (OCT) Analysis of Retinal Nerve Fiber Layer (RNFL)

Figure 3:
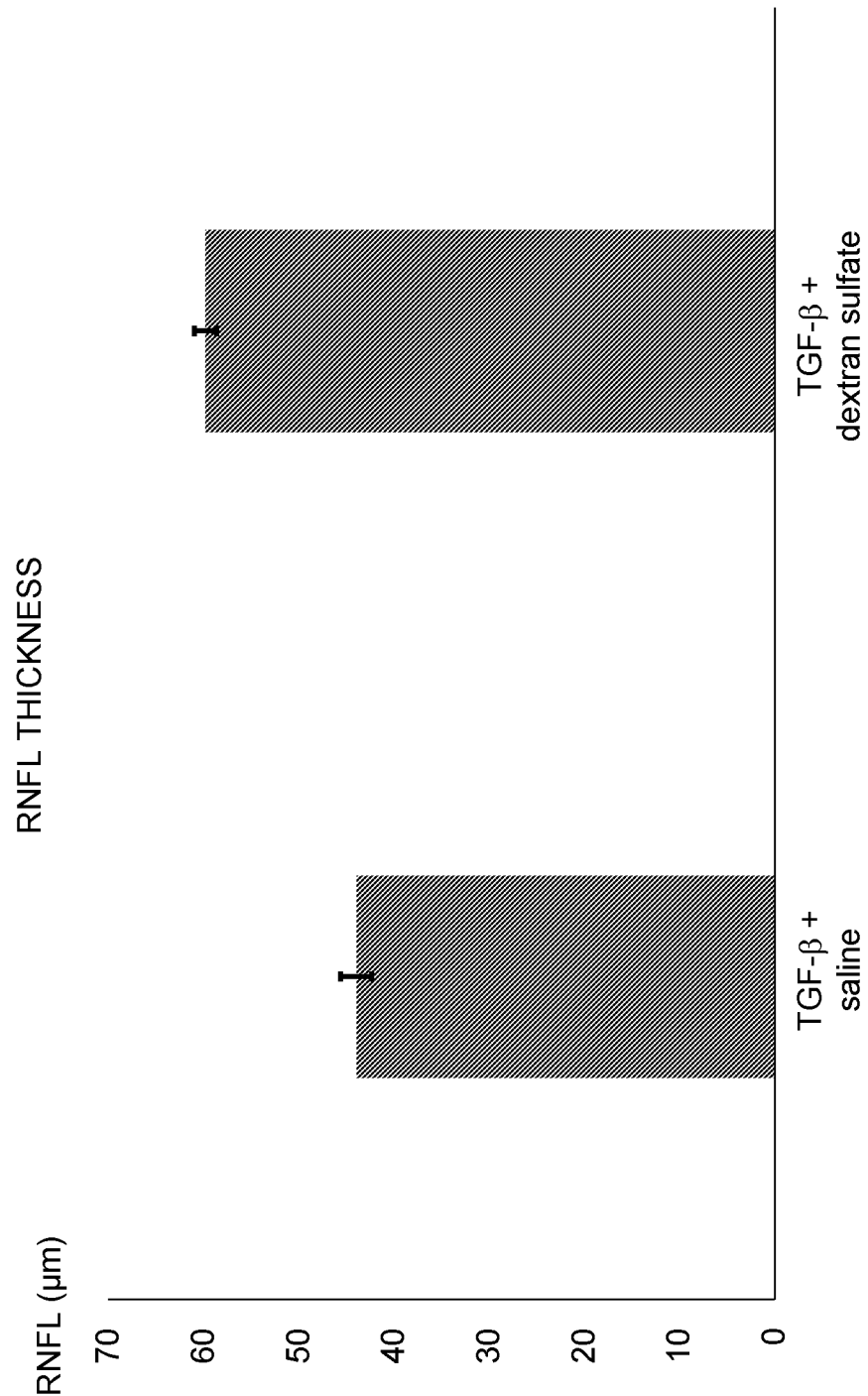
FIG. 3 illustrates changes in retinal nerve fiber layer (RNFL) thickness in subjects suffering from POAG and treated with saline control or dextran sulfate according to the embodiments.
Figure 11:
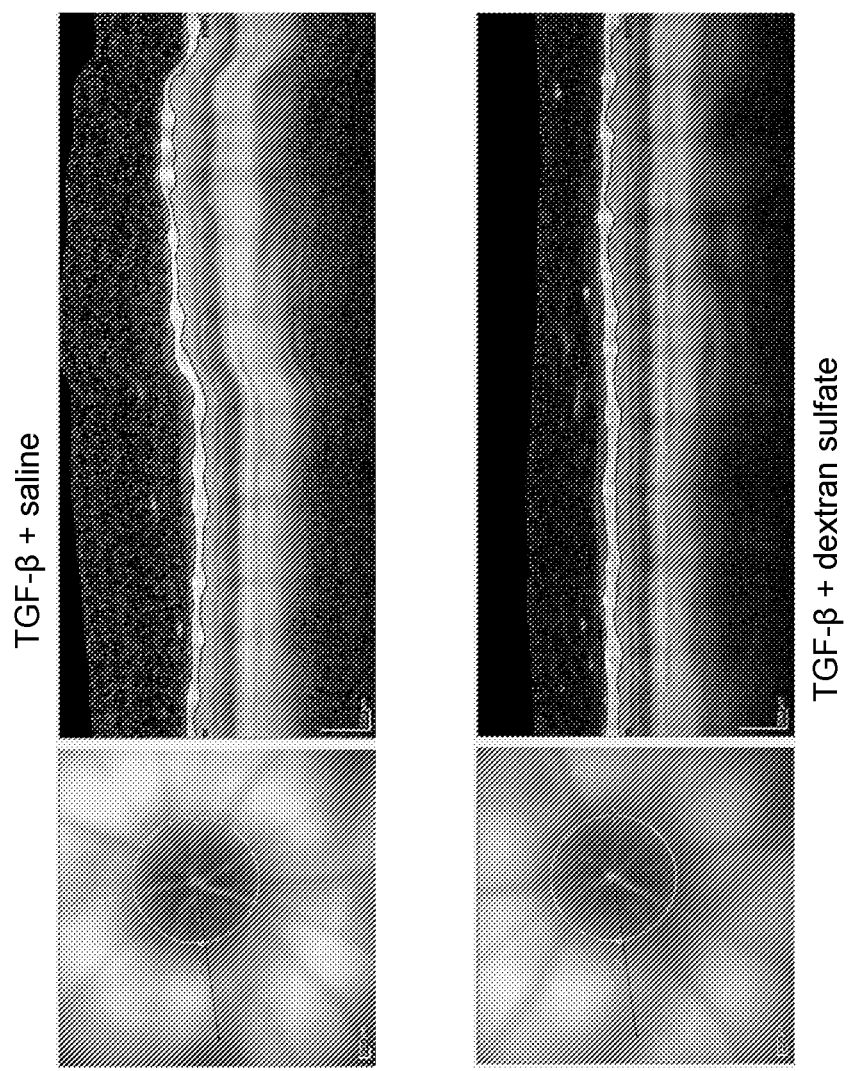
FIG. 11 illustrates results of an optical coherence tomography (OCT) analysis of RNFL.

The RNFL comprises axons belonging to the RGC and is lost concomitantly with the loss of the RGC cell body. The RNFL was preserved after dextran sulfate treatment compared to saline treatment (FIGS. 3 and 11), suggesting a neuroprotective effect of dextran sulfate. This neuroprotective effect may be via a direct or indirect effect due to the lowered IOP.

Anterior Segment Imaging of the Angle

Figure 4:
FIG. 4 illustrates anterior segment imaging of the iridocorneal angle in subjects suffering from POAG and treated with saline control or dextran sulfate according to the embodiments.

In both the saline and dextran sulfate treated eyes, the iridocorneal angle remained 'open' demonstrating that IOP increases were not due to angle closure, see FIG. 4.

Trabecular Meshwork (TM) Scarring

Figure 5:
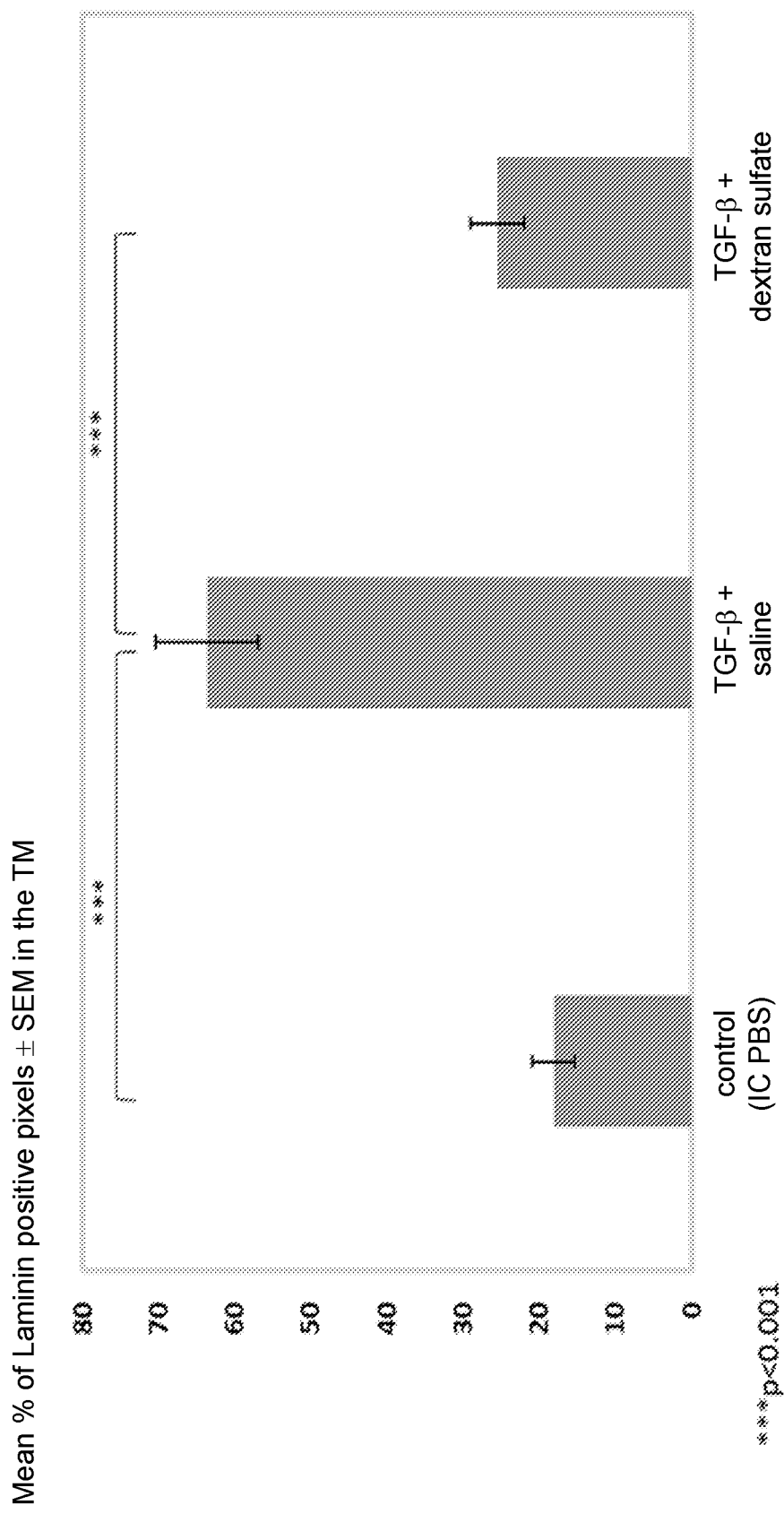
FIG. 5 illustrates changes in laminin immunoreactivity in the angle in subjects suffering from POAG and treated with saline control or dextran sulfate according to the embodiments.
Figure 6:
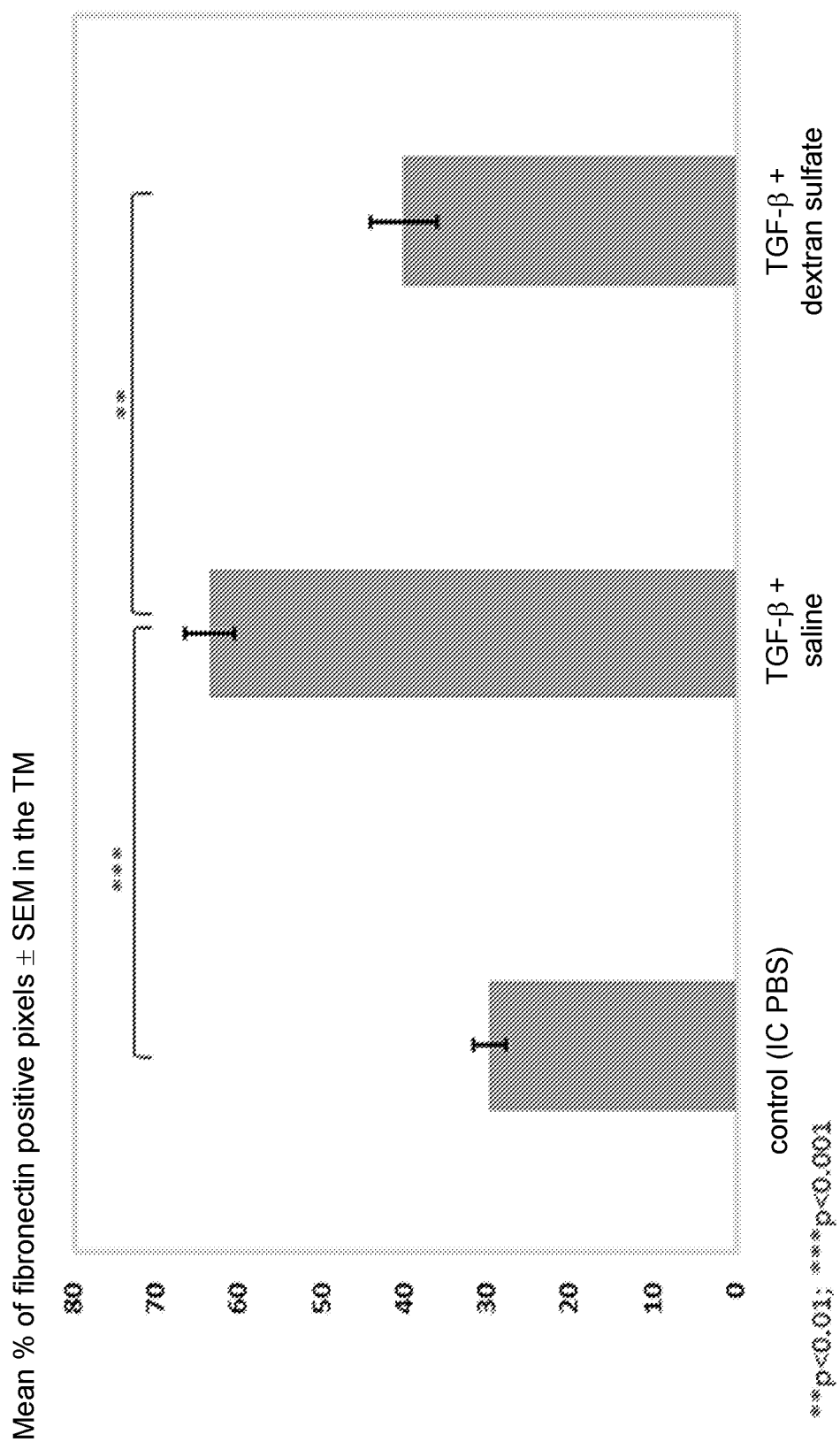
FIG. 6 illustrates changes in fibronectin immunoreactivity in the angle in subjects suffering from POAG and treated with saline control or dextran sulfate according to the embodiments.

Dextran sulfate treatment significantly attenuated TM scarring, as evidenced by significantly reduced ($P<0.001$ laminin; $P<0.01$ fibronectin) levels of immunoreactive laminin (FIG. 5) and fibronectin (FIG. 6) in the angle.

Body Weight

Figure 7:
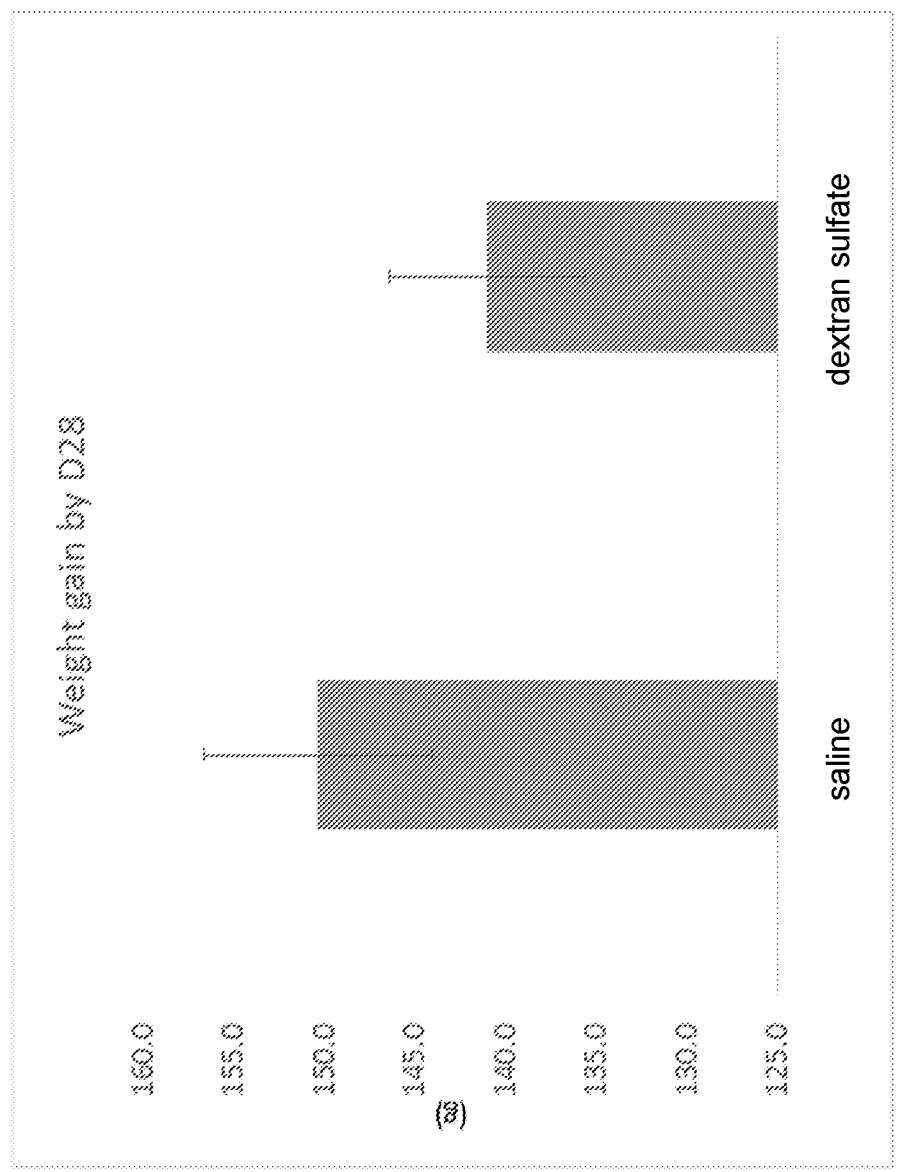
FIG. 7 illustrates differences in body weight in subjects suffering from POAG and treated with saline control or dextran sulfate according to the embodiments.

The rats in the dextran sulfate treated group were more active. When body weight was measured in both groups there was a small but non-significant difference due to the dextran sulfate-treated animals gaining less weight over the treatment period than did saline treated animals (FIG. 7).

Conclusions

Dextran sulfate treatment led to rapid and reproducible restoration of normal IOP in glaucomatous eyes. Restoration of normal IOP levels was associated with preservation of RGC in the retinal as evidenced by maintained RGC counts and a preservation of RNFL thickness in eyes from dextran sulfate treated rats. The fall in IOP probably resulted from dissolution of established TM scar elements as levels of laminin and fibronectin were significantly lower in the angle of dextran sulfate treated rats.

The clinical implications of the observations are as follows. Patients with glaucoma are currently treated by daily eye drops of drugs that lower IOP either by limiting ocular fluid production or increasing ocular fluid outflow. These treatments have poor compliance and, consequently, IOP is imperfectly controlled, leading to progressive vision loss in most patients. A treatment that reverses the ocular pathology leading to vision loss and significantly improves IOP control would be highly valuable. Dextran sulfate according to the embodiments enables such a treatment leading to normalized IOP, preservation of RGCs and RNFL and dissolution of TM scar elements.

Material and Methods

Study Design

Glaucoma was induced in adult male Sprague Dawley rats by repeat twice weekly intracameral (IC) injections of transforming growth factor-β (TGF-β) to increase intraocular pressure (IOP). Sustained increases in IOP (after two weeks) leads to death of retinal ganglion cells (30-40%). Dextran sulfate (Tikomed AB, Sweden, WO 2016/076780) was administered at 15 mg/kg by daily subcutaneous injection from the start of the experiment to assess RGC protection compared to controls.

Group 1 n=12 rats; 24 eyes IOP+IC TGF-β (twice weekly for 28 days) between day 0 and day 28+ daily subcutaneous administration of dextran sulfate from day 14 to day 28.

Group 2 n=8 rats; 16 eyes IOP+IC TGF-β (twice weekly for 28 days) between day 0 and day 28+ daily subcutaneous administration of vehicle (saline) from day 14 to day 28.

Group 3 n=8 rats; 8 eyes IOP+intact (uninjured eye) and 8 eyes IOP+IC phosphate-buffered saline (PBS) daily for 28 days.

Measured End-Points

IOP twice weekly throughout study from day 0 to day 28;

Immunohistochemistry for counting RGC that are immunoreactive for brain-specific homeobox/POU domain protein 3A (Brn3a) at day 28 (RGC survival);

Immunohistochemistry for laminin and fibronectin to evaluate scarring in the trabecular meshwork at day 28 in Groups 1 and 2;

Anterior segment and OCT imaging at day 28 to examine the angle and the thickness of the retinal nerve fiber layer comprising RGC axons; and Body weight at day 28.

Animals and Surgery

Sixteen 8 to 10 week-old male 175-200 g Sprague Dawley rats (Charles River, Kent, UK), housed with free access to food and water under a 12 h dark/light cycle, were used for these experiments. Surgery was performed at the Biomedical Services Unit at the University of Birmingham in accordance with the Home Office guidelines set out in the 1986 Animal Act (UK) and the ARVO Statement for the Use of Animals in Ophthalmic and Vision Research. All ocular surgical procedures and IOP measurements were completed under inhalational anesthesia using 2-5% isofluorane/95% $O_2$ (National Vet Supplies, Stoke, UK) at a flow rate of 1.5 L/min. The post-operative welfare of all rats was monitored closely.

At day 0, one self-sealing incision was made through the cornea into the anterior chamber of both eyes using a 15° disposable blade enabling repeated, twice a week (bi-weekly), 3.5 µl IC injections (every Monday and Thursday) through the tunnel generated using self-made disposable sterile glass micropipettes (Harvard Apparatus, Kent, UK) for 28 days of active human recombinant TGF-β1 (5 ng/µl; Peprotech, London, UK).

IOP Measurements

Using an iCare Tonolab rebound tonometer (Icare, Helsinki, Finland), IOP was recorded bi-weekly between 9-11 am for the duration of each experiment to avoid confounding the readings with circadian variability. Immediately after induction of anesthesia with 5% isoflurane, six rebound measurements were taken with the tonometer from the central cornea on each measurement occasion to give an overall average IOP measurement (mmHg) and all graphical data points represent the mean±SEM of 3 readings (of 6 rebounds each) taken sequentially to ensure accurate measurements.

OCT and Anterior Segment Imaging

Optical coherence tomography allows in vivo measuring of retinal thickness with RNFL being a surrogate measure of RGC density. OCT retinal nerve fiber layer analysis was performed at day 28 on all rats while under inhalation anesthesia using a Spectralis HRA3 confocal scanning laser ophthalmoscope (Heidelberg Engineering). Anterior segment images on the angle were taken together with OCT images of the retina around the optic nerve head. In-built software was used to segment the images and quantify the RNFL thickness.

Tissue Preparation for Immunohistochemistry (IHC)

Rats were killed by exposure to increasing concentrations of $CO_2$ and transcardially perfused with 100 ml of phosphate-buffered saline (PBS) to wash out blood before further perfusion with 100 ml 4% paraformaldehyde (PFA) in PBS at pH 7.4. Dissected eyes for IHC were post-fixed by immersion in 4% PFA in PBS for 2 h at 4° C. before cryoprotection by immersion in increasing concentrations of sucrose solutions (PBS with 10%, 20% and 30% sucrose; all from Sigma, Poole, UK) for 24 h each at 4° C. then embedded in optimal cutting temperature embedding medium (Thermo Shandon, Runcorn, UK) in peel-away mold containers (Agar Scientific, Essex, UK). Eyes immersed in optimal cutting temperature embedding medium were rapidly frozen in crushed dry ice before storage at −80° C. and later sectioned in the parasagittal plane through the optic nerve head at −22° C. using a Bright cryostat microtome (Bright, Huntingdon, UK) at a thickness of 15 μm. Sections were mounted on positively charged glass slides (Superfrost plus; Fisher Scientific, Pittsburgh, USA), left for 2 h to dry at 37° C. and stored at −20° C.

Immunohistochemistry

Frozen sections were left to thaw for 30 min before 3×5 min washing in PBS followed by a 20 min permeabilization with 0.1% Triton X-100 (Sigma). Sections were blocked for 30 min in 0.5% bovine serum albumin (BSA) and 0.3% Tween-20 (all from Sigma) in PBS and were incubated overnight in primary antibody (Table 1) before washing 3×5 min in PBS and incubating for 1 h at room temperature (RT; 20-25° C.) with secondary antibody (Table 1). Sections were then washed 3×5 min in PBS and mounted in Vectorshield mounting medium containing 4',6-diamidino-2-phenylindole (DAPI) (Vector Laboratories). Control tissue sections incubated with secondary antibody alone were all negatively stained (not shown).

TABLE 1

Antibodies used in immunohistochemistry

| Antigen | Dilution | Supplier | Catalogue No. | To identify |
| --- | --- | --- | --- | --- |
| Laminin | 1:200 | Sigma | L9393 | TM fibrosis |
| Fibronectin | 1:200 | Sigma | F3648 | TM fibrosis |
| RPBMS* | 1:200 | Millipore | ABN1362 | RGC |
| Goat Anti-mouse IgG Alexa Fluor 594 | 1:400 | Molecular Probes | A-11032 | Secondary IgG for ED1 primary antibody |

TABLE 1-continued

Antibodies used in immunohistochemistry

| Antigen | Dilution | Supplier | Catalogue No. | To identify |
| --- | --- | --- | --- | --- |
| Goat Anti-rabbit IgG, Alexa Fluor 488 | 1:400 | Molecular Probes | A-21206 | Secondary IgG for rabbit primary antibodies |

*RNA-binding protein with multiple splicing

Quantification of Immunohistochemistry

After immunofluorescence staining, sections were viewed on a Zeiss Axioplan 2 epi-fluorescent microscope (Carl Zeiss Ltd) and images captured using the same exposure times for each antibody using a Zeiss AxioCam HRc. IHC was quantified according to the methods previously described [1]. Briefly, the region of interest used for quantitation of TM fibrosis was defined by a quadrant of the same prescribed size for all eyes/treatments within the TM, and ECM deposition was quantified within this defined quadrant of the TM and the % immunofluorescent pixels above a standardized background threshold calculated using ImageJ software (National Institutes of Health, USA). For each antibody, the threshold level of brightness in the area of the TM was set using intact untreated eye sections to define the reference level for test group analysis of pixel intensity. Images were assigned randomized numbers to ensure blinding of treatment groups during quantification by the assessor.

For quantification of RGC in retinal sections, RPBMS$^+$/DAPI$^+$ RGC were counted in 15 μm thick parasagittal sections of retina from a 250 μm linear portion from the ganglion cell layer at either side of the optic nerve. Four retinal sections from each eye in the control and treatment groups were quantified. Images were assigned randomized numbers to ensure blinding of treatment groups during quantification by the assessor.

Statistics

All statistical analyses were performed using SPSS 20 (IBM, USA). Normal distribution tests were carried out to determine the most appropriate statistical analysis to compare treatments. Statistical significance was determined at $p<0.05$. IOP data, TM fibrosis and RGC survival were tested for significant differences using Student t test or 1-way ANOVA for >2 Group comparisons±SEM and are given in the text or displayed graphically as mean±SEM.

Example 2—Investigating the Vascular Effects of Dextran Sulfate in a Mouse Model of Neovascular Age-Related Macular Degeneration (nAMD)

Pathologic angiogenesis in the eye can lead to severe visual impairment. Accordingly, drugs that induce neovascularization or enhance neovascular pathologies are strongly contraindicated.

The mouse laser-induced choroidal neovascularization (CNV) model has been a crucial mainstay model for neovascular age-related macular degeneration (AMD) research. By administering targeted laser injury to the retinal pigment epithelium (RPE) and Bruch's membrane, the procedure induces angiogenesis, modeling the hallmark pathology observed in neovascular AMD. First developed in non-human primates, the laser-induced CNV model has come to be implemented into many other species, the most recent of which being the mouse. The model can be applied to study many aspects of ocular neovascular biology, such as molecular mechanisms, the effect of genetic manipulations, and drug treatment effects.

Results

Figure 8:
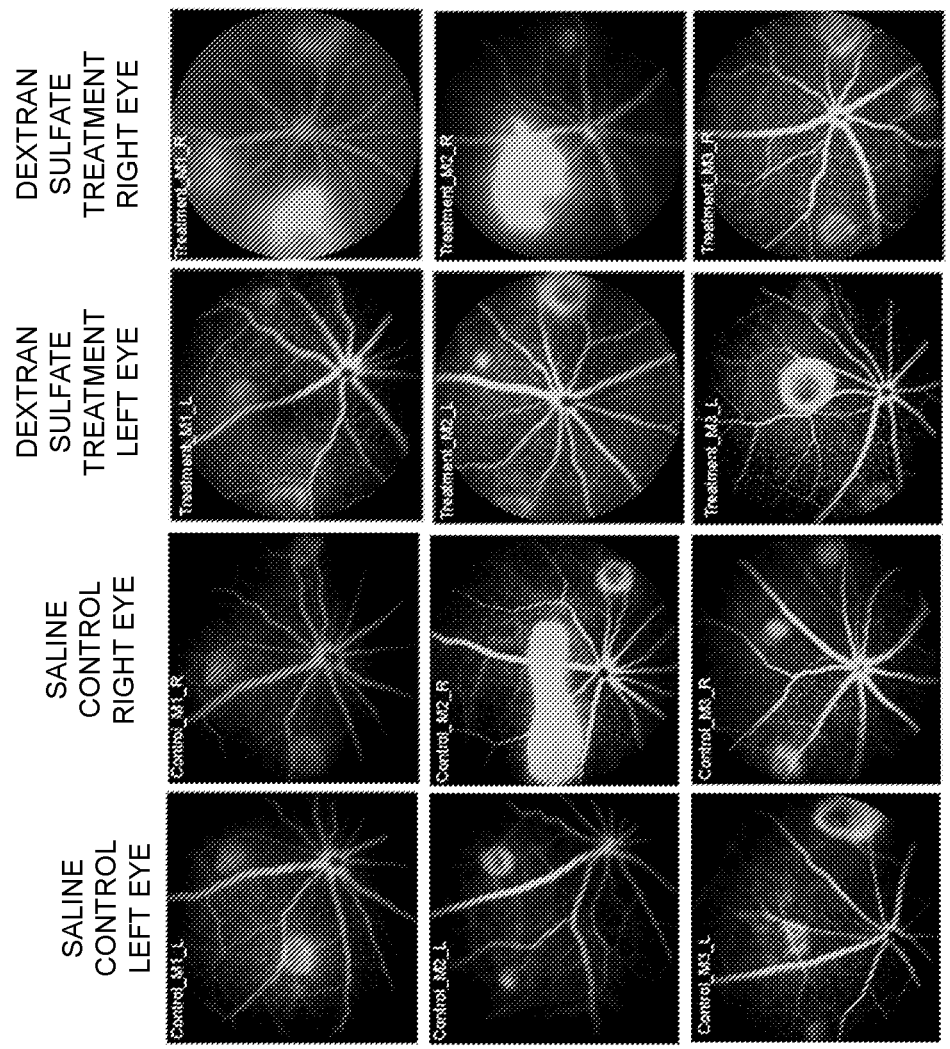
FIG. 8 are representative fluorescein angiography images of subjects suffering from POAG and treated with saline control or dextran sulfate according to the embodiments.

Visualization of Choroidal Neovascular Membrane in Fundus Fluorescein Angiography Retinal blood vessels were clearly visualized in fundus fluorescein angiography. Choroidal neovascularizations were shown as patches of hyperfluorescence. FIG. 8 shows representative fluorescein angiography images from each mouse. There were variations in the size of CNV in different eyes. Occasionally, two CNVs were merged together with intensive fluorescein leakage, these were excluded from quantitative analyses. Visual examination of fundus fluorescein angiography images did not show significant difference in the size of CNV between the two groups.

CNV Analysis

Seventy-two laser burn spots were conducted in each group. The CNVs that were merged from two laser spots or over-sized (>100000 $\mu m^2$) due to subretinal haemorrhage or severe inflammation were excluded from the final data analysis. Table 2 summaries the number of CNVs included in the final data analysis.

TABLE 2

CNV in each experimental group

| Group | Treatment | No. of Laser spot | No. of CNV for data analysis |
|---|---|---|---|
| Group 1 | Dextran sulfate | 72 | 58 |
| Group 2 | Saline | 72 | 56 |

Quantification of Neovascularization Using Isolectin B4

Figure 9:
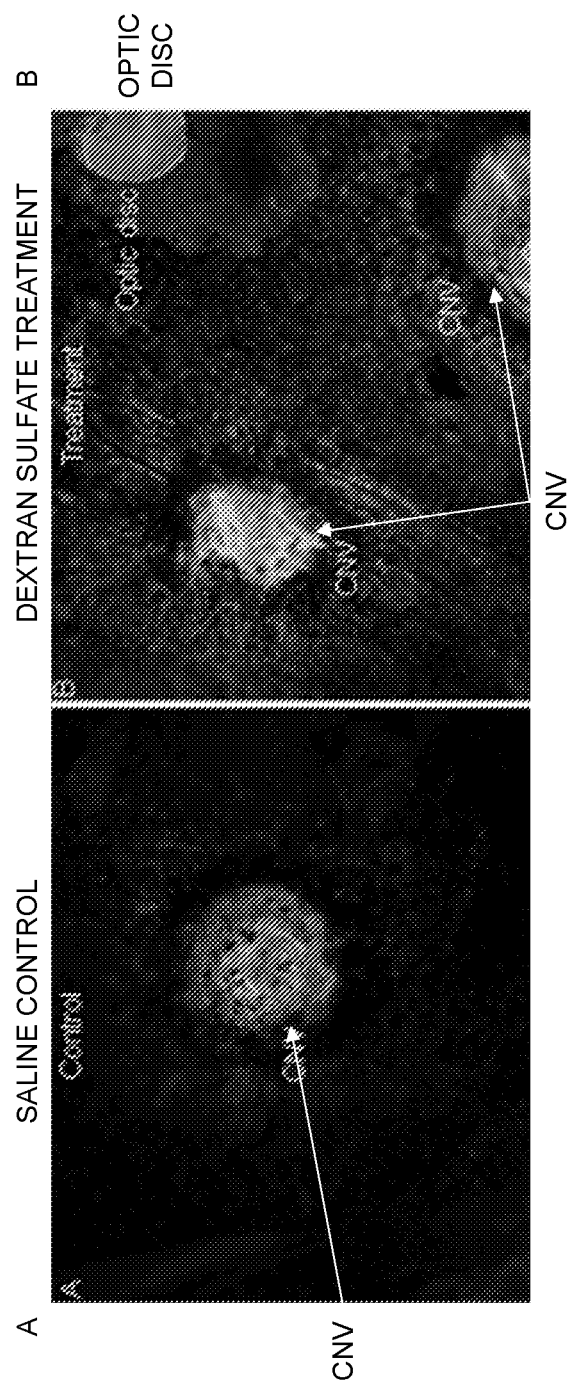
FIG. 9 illustrates choroidal neovascularization using isolectin B4 staining. The representative images of neovascularization in control (FIG. 9A) and treatment (FIG. 9B) group.
Figures 9C, 10C:
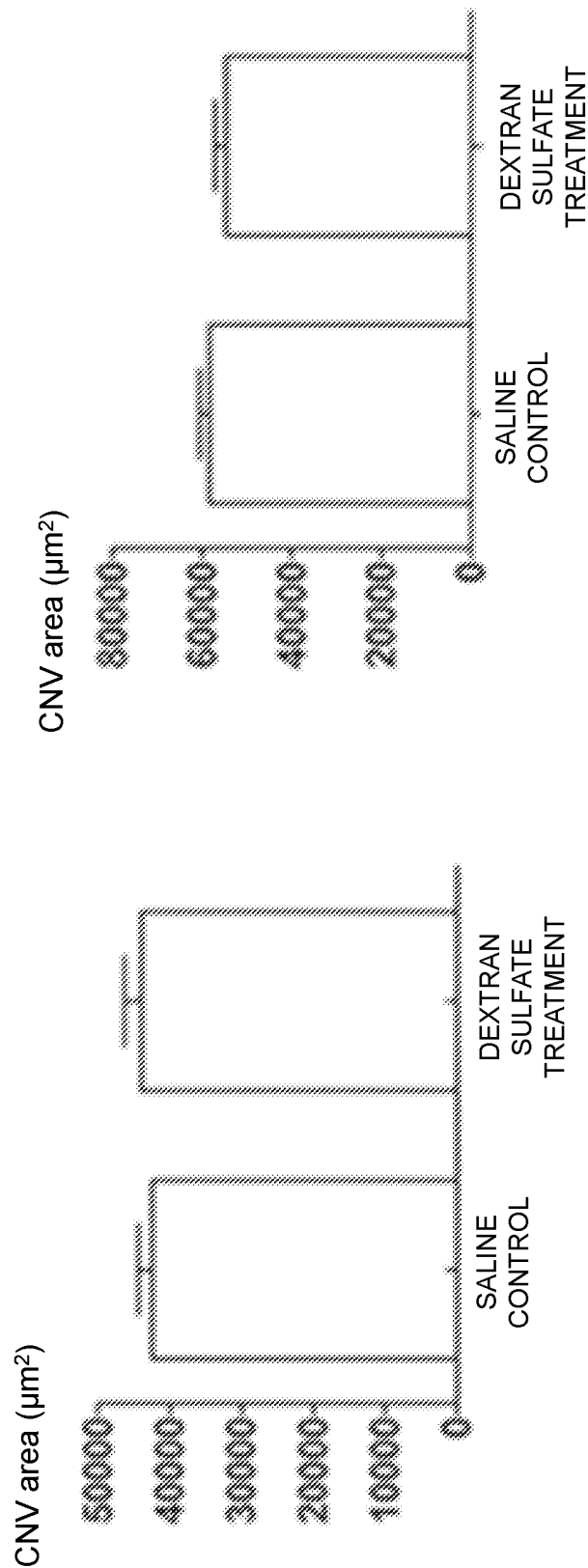
(FIG. 9C): Bar figure shows the average neovascular areas.
(FIG. 10C): Bar figure shows the average neovascular areas.

Isolectin B4 (*Griffonia simplicifolia* lectin I-isolectin B4) has been used as markers for retinal blood vessels as it is expressed in the endothelial cells. It also is expressed in activated microglia and infiltrating macrophages in the retina. The average isolectin B4 positive area was 43972±2302 $\mu m^2$ in the test compound treatment group, and 42432±2015 $\mu m^2$ in the saline control group (FIG. 9). There was no statistical difference between the two groups in lectin B4$^+$ lesions.

Quantification of New Blood Vessel area Using Collagen IV

Figure 10:
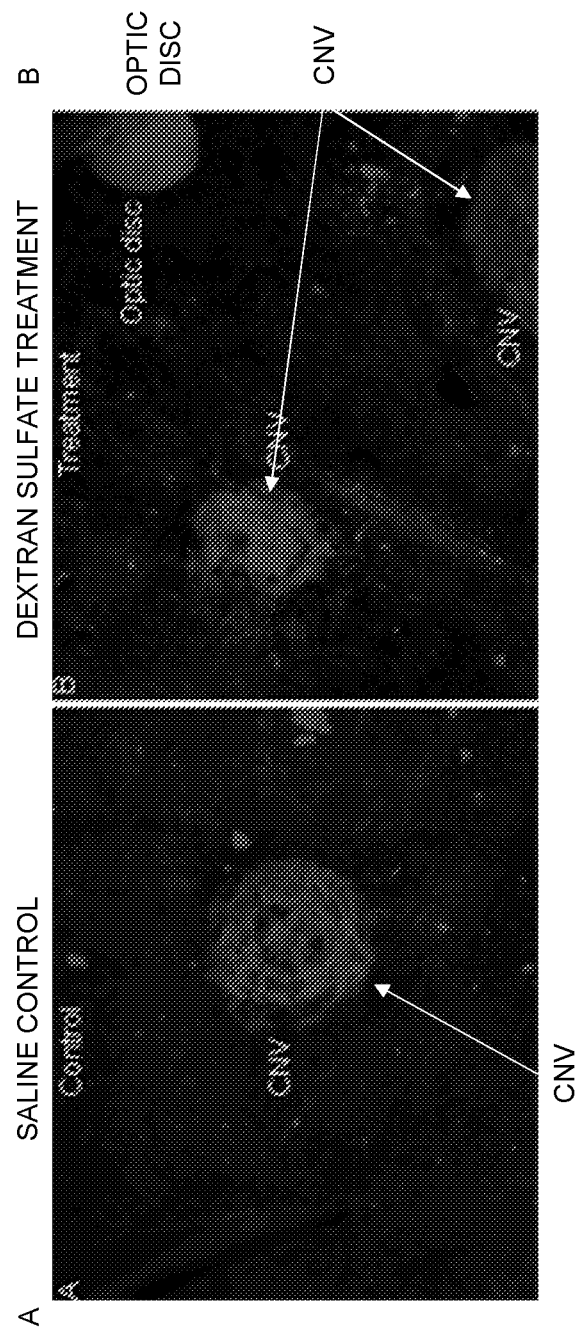
FIG. 10 illustrates choroidal neovascularization using collagen IV staining. The representative images of neovascularization in control (FIG. 10A) and treatment (FIG. 10B) group.

Collagen IV forms the laminar layer of the blood vessel matrix. Therefore it has been used to demonstrate new blood vessels. In the dextran sulfate treatment group, the means of area of new blood vessels was 54681±2378 $\mu m^2$, compared to 58215±2293 $\mu m^2$ in the vehicle (saline) treatment control group (FIG. 10). There was no statistical significant difference between the two groups.

Conclusions

The results indicate that dextran sulfate has neither anti-angiogenic nor pro-angiogenic effects on the laser-induced CNV at the dose of 0.6 mg/ml per day. This indicates applicability of dextran sulfate to ocular indications.

Material and Methods

Mice

Twenty-four 10 to 12-week old C57BL/6J mice were purchased from Biological Service Unit at Queen's University Belfast. All mice were housed with free access to water and chow diet and exposed to a 12-hour dark/light cycle. All procedures concerning the use of animals in this study were performed according to the Association for Research in Vision and Ophthalmology (ARVO) Statement for the Use of Animals in Ophthalmic and Vision Research and under the regulations of the Animals (Scientific Procedures) Act 1986 (UK). The protocol was approved by the Animal Welfare & Ethics Board of Queen's University Belfast.

Test Compound

The test compound dextran sulfate (Tikomed AB, Sweden, WO 2016/076780) was provided at a concentration of 6 mg/ml. Sterile saline (purchased from Aqupharm) was used to dilute the compound to the working concentration (0.6 mg/ml).

CNV Induction

Mice were anaesthetized with an intraperitoneal injection of 75 mg/kg ketamine and 7.5 mg/kg xylazine. The pupils were dilated with 1% atropine and 2.5% phenylephrine (Bausch & Lomb). To induce CNV, the rupture of Bruch's membrane-choroid was achieved by laser photocoagulation using the HGM Elite 532 Green Laser (Litechnica Ltd, Middlesex, UK) with the spot size of 100 µm, 250 mW power and 100 msec duration. The laser spots were placed between retinal vessels and 2 to 3 disc-diameter away from the optic disc. The formation of a bubble at the site of laser application indicates the successful rupture of Bruch's membrane. Only laser burns in which a bubble was produced were included in this study. In addition, the laser burns that showed severe subretinal haemorrhage during CNV induction were excluded from the study. Three laser burns were applied to each retina.

Drug Administration

Immediately after CNV induction, all mice were injected subcutaneously with 500 µl of dextran sulfate or saline. The injection was repeated once daily for 9 days post laser-CNV induction. The detailed treatments are shown in Table 3.

TABLE 3

Experimental groups

| Group | Treatment | Method | Concentration, volume |
|---|---|---|---|
| Group 1 (G1) | Dextran sulfate | Subcutaneous, once daily | 0.6 mg/ml, 500 µl |
| Group 2 (G2) | Saline | Subcutaneous, once daily | 500 µl |

Fluorescent Angiography

On day 10 post-CNV induction, 3 mice from each group were randomly selected for fundus fluorescein angiography. Mice were anaesthetized with an intraperitoneal injection of 75 mg/kg ketamine and 7.5 mg/kg xylazine. The pupils were dilated with 1% atropine and 2.5% phenylephrine. 100 µl of 1% sodium fluorescence was injected intraperitoneally. Fundus images were captured using the Micron IV Retinal Imaging Microscope (Phoenix Research Labs). Mice were sacrificed after fluorescein angiography and eyes were collected.

Sample Collection

On day 10 post-CNV induction, all mice were sacrificed and eyes were carefully removed. All eyes were fixed in 2% paraformaldehyde/PBS (Sigma-Aldrich, Dorset, UK) for 2 h at room temperature and then washed and stored in PBS at 4° C. RPE-choroid-sclera wholemounts were prepared using the protocol described [2, 3]. Briefly, the anterior segment of the eye, including the cornea, ciliary body, iris and the lens were removed. Five vertical cuts were made to the eye cup, and the retinal tissue was then carefully removed. The extra ocular tissues, including conjunctiva and ocular muscles were carefully removed from the eye-cup (containing RPE/choroid/sclera). The RPE/choroidal/sclera wholemounts were further processed for *Griffonia simplicifolia* lectin 1-isolectin B4 and collagen IV immunostaining.

Immunostaining of RPE/Choroidal/Sclera Wholemounts

CNV was detected using the well-established isolectin B4 and collagen IV labelling technique. Isolectin B4 labels both infiltrating macrophages and vascular endothelial cells. Collagen IV labels the basal lamina of blood vessels. Both markers have been used widely to detect CNV.

RPE/choroidal/sclera wholemounts were permeablized with 0.5% Triton X-100/PBS for 1 h at room temperature. The samples were then blocked with 10% BSA in 0.5% Triton X-100/PBS for 1 h and incubated with biotinylated *Griffonia simplicifolia* lectin 1-isolectin B4 (GSL Isolectin B4, 1:50, Vector Laboratories Ltd, UK) and collagen IV (1:50, BIO-RAD, UK) overnight at 4° C. After thorough washing in PBS (10 minutes×3), samples were incubated with streptavidin-fluorescein isothiocyanate (FITC) (1:100, Vector laboratories, UK) and goat anti rabbit AF594 (1:100, Invitrogen, UK) for two hours at room temperature. Samples were flat-mounted on glass slides with Vectashield Mounting Medium (Vector Laboratories Ltd, UK) and observed by fluorescent microscopy.

Image Acquisition and Analysis

Lecia fluorescent microscope was used to acquire images from above prepared RPE-choroidal/sclera wholemount samples. A 10× objective lens was used to allow capturing the whole area of a CNV. The imaging software ImageJ was used to analyze the images. To measure the size of CNV, the border of CNV was outlined manually and the size was automatically calculated using Image J software.

Statistical Analysis

All data (the size of CNV in each group) were expressed as mean±SEM. Student t test was used to compare the difference between the dextran sulfate group and the saline control group.

Study Design

24 C57BL/6J mice (10~12 weeks old) were used in this study. The mice were randomized into two groups (12 mice per group)

Group 1: dextran sulfate treatment (500 µl of 0.6 mg/ml of dextran sulfate in saline), subcutaneous injection, once daily after CNV induction for 9 days.

Group 2: vehicle treatment (500 µl saline), subcutaneous injection, once daily after CNV induction for 9 days.

On day 10 post CNV induction, 3 mice from each group were randomly selected for fundus fluorescein angiography. All mice were sacrificed on day 10 post CNV induction. Eyes were collected and processed for immunohistochemistry investigations.

Example 3—Analysis of Changes in Gene-Expression Induced by Dextran Sulfate in Schwann Cells Results Expression Analysis of Schwann Cells Genes not expressed in the Schwann cells were removed prior to data analysis. The 'below expression' level was set at 5 for the log 2 transformed expression values. This left 15,842 unique probes to analyze in the Schwann cell cultures. In the next step of the analysis, three sets of data (comparison of D0 control to D2 control samples; comparison of D0 control to D2 dextran sulfate treated samples; comparison of D2 control to D2 dextran sulfate treated samples) were analyzed to establish the effect of the CM on the cells and the relative changes induced by dextran sulfate.

585 genes were differentially expressed in Schwann cell cultures when comparing the D0 control to the D2 control samples. The molecular functions influenced by these genes relate to cellular movement (1.14E-07-2.49E-03); cell morphology (5.56E-07-2.36E-03); cellular development (7.3E-06-2.48E-03); cellular growth and proliferation (7.3E-06-2.48E-03); cellular assembly and organization (1.23E-05-2.36E-03); cellular function and maintenance (1.23E-05-2.47E-03); cell death and survival (1.53E-05-2.51E-03); lipid metabolism (8.14E-05-1.6E-03); small molecule biochemistry (8.14E-05-1.6E-03); molecular transport (1.18E-04-2.29E-03); protein trafficking (1.62E-04-1.6E-03); carbohydrate metabolism (3.22E-04-1.78E-03); gene expression (3.98E-04-2.2E-03); cell signaling (4.39E-04-2.25E-03); cell-to-cell signaling and interaction (5.05E-04-2.48E-03); cellular compromise (7.69E-04-1.58E-03); cell Cycle (1.12E-03-1.8E-03); amino acid metabolism (1.6E-03-1.6E-03); and nucleic acid metabolism (1.6E-03-1.6E-03).

The values presented above are p-values representing the statistical significance of the association of these genes with the different pathways. The two p values represent the lower and upper limits of the statistical significance observed ($p<0.05$ is significant).

Dextran sulfate induced differential expression in Schwann cell culture of 1244 genes as assessed when comparing the D0 control to the D2 dextran sulfate treated samples. The molecular functions influenced by these genes relate to cell morphology (1.43E-08-8.39E-04); cellular movement (1.4E-07-9.6E-04); post-translational modification (3.93E-07-6.71E-05); protein synthesis (3.93E-07-1.08E-04); protein trafficking (3.93E-07-1.26E-06); cell death and survival (2.13E-06-8.65E-04); cellular assembly and organization (7.46E-06-8.24E-04); DNA replication, recombination, and repair (7.46E-06-7.46E-06); cellular function and maintenance (9.53E-06-6.46E-04); gene expression (1.27E-05-4.92E-04); cellular development (1.29E-05-9.06E-04); cellular growth and proliferation (1.29E-05-9.06E-04); cell-to-cell signaling and interaction (1.97E-05-8.81E-04); amino acid metabolism (4.22E-05-8.24E-04); small molecule biochemistry (4.22E-05-8.24E-04); lipid metabolism (4.81E-05-3.64E-04); molecular transport (3.64E-04-3.64E-04); and cell cycle (4.53E-04-4.86E-04).

Dextran sulfate induced differential expression in Schwann cell culture of 700 genes as assessed when comparing the D2 control to the D2 dextran sulfate treated samples. The molecular functions influenced by these genes relate to cell morphology (1.49E-07-5.62E-03); cellular assembly and organization (1.49E-07-5.95E-03); cellular movement (7.24E-07-6.06E-03); cell death and survival (9.41E-06-5.95E-03); amino acid metabolism (2.56E-05-3.7E-03); post-translational modification (2.56E-05-1.05E-03); small molecule biochemistry (2.56E-05-3.7E-03); cell-to-cell signaling and interaction (5.05E-05-5.76E-03); gene expression (7.18E-05-4.94E-03); cell cycle (1.06E-04-5.95E-03); cellular development (1.06E-04-5.95E-03); cellular function and maintenance (1.96E-04-5.95E-03); cellular growth and proliferation (2.35E-04-5.95E-03); DNA replication, recombination and repair (2.75E-04-5.95E-03); cell signaling (5.92E-04-2.54E-03); cellular comprise (6.26E-04-6.26E-04); lipid metabolism (6.26E-04-1.85E-03); molecular transport (6.26E-04-5.95E-03); protein synthesis (1.05E-03-1.93E-03); cellular response to therapeutics (1.85E-03-1.85E-03); protein trafficking (2.66E-03-5.95E-03); and RNA post-transcriptional modification (4.32E-03-4.32E-03).

The mechanistic molecular network model simulates the effect of the differentially regulated molecules by dextran sulfate enabling the functional consequences of these changes to be evaluated. The in silico model indicated that dextran sulfate inhibits neuronal cell death; apoptosis; and synthesis of protein and activates angiogenesis; migration of cells; cell viability; cell survival; cell movement; proliferation of cells; differentiation of cells; cellular homeostasis; cell cycle progression; cell transformation; and expression of RNA.

Table 4 summarizes the results of the gene expression changes in the cultured Schwann cells.

The Effect of Dextran Sulfate on Cell Adhesion

One of the strong noticeable phenotypic effects of dextran sulfate was the effect on cell adhesion.

The analysis of gene expression indicated that this is due to the effect of dextran sulfate on the expression of enzymes that regulate cell attachment including metallopeptidases, also referred to as matrix metalloproteinases (MMPs), see Table 5.

The aggregate effect of these molecules on the pathways regulating cell movement and attachment in Schwann cells (17 molecules, see Table 5) was such that cell adhesion would be inhibited while cell movement would be activated.

TABLE 5

Molecules of the pathway regulating cell movement and attachment in Schwann cells

| Symbol | Entrez gene name | Location | Type(s) |
| --- | --- | --- | --- |
| A2M | alpha-2-macroglobulin | Extracellular Space | transporter |
| ADAM10 | ADAM metallopeptidase domain 10 | Plasma Membrane | peptidase |
| ADAM23 | ADAM metallopeptidase domain 23 | Plasma Membrane | peptidase |
| ADAMTS9 | ADAM metallopeptidase with thrombospondin type 1 motif 9 | Extracellular Space | peptidase |
| CDH11 | cadherin 11 | Plasma Membrane | other |
| CSF3 | colony stimulating factor 3 | Extracellular Space | cytokine |
| FAS | Fas cell surface death receptor | Plasma Membrane | transmembrane receptor |
| HIF1A | hypoxia inducible factor 1 alpha subunit | Nucleus | transcription regulator |
| IL6 | interleukin 6 | Extracellular Space | cytokine |
| IL15 | interleukin 15 | Extracellular Space | cytokine |
| LUM | lumican | Extracellular Space | other |
| MMP3 | matrix metallopeptidase 3 | Extracellular Space | peptidase |
| POSTN | periostin | Extracellular Space | other |
| RECK | reversion inducing cysteine rich protein with kazal motifs | Plasma Membrane | other |
| SERPINA3 | serpin family A member 3 | Extracellular Space | other |
| TNC | tenascin C | Extracellular Space | other |
| VCAM1 | vascular cell adhesion molecule 1 | Plasma Membrane | transmembrane receptor |

TABLE 4

Overall pattern of gene expression changes in Schwann cells

| | abolished nutrient effect | enhanced response to nutrients | new effect induced by dextran sulfate | not different from control | total |
| --- | --- | --- | --- | --- | --- |
| no effect | 21 | | | | 21 |
| significant downregulation | 1 | 122 | 352 | 42 | 517 |
| significant upregulation | 13 | 441 | 74 | 373 | 901 |
| total | 35 | 563 | 426 | 415 | 1439 |

21 genes that have altered expression in the Control cultures in the two days did not show any changes at all in the dextran sulfate treated cultures during the same two days. 1 gene that had increased expression in the control cultures was downregulated in the dextran sulfate treated cultures during the same two days. 13 genes that were downregulated in the control cultures were upregulated in the dextran sulfate treated cultures during the two days. 122 genes were significantly downregulated by growth factors in the culture medium and this downregulation was even stronger in the dextran sulfate treated cultures. 441 genes were upregulated in the Control cultures and the addition of dextran sulfate made this upregulation significantly stronger.

This finding led to the re-assessment of all molecular interactions that affect cell attachment and adhesion related molecules and their effect on cellular attachment in Schwann cells. The full list of the 217 attachment-related molecules (197 genes and 20 drugs) are presented below:

ACE2, ACP1, ADAM15, ADGRB1, ADGRE2, ADIPOQ, AG490, AMBN, ANGPT1, ANTXR1, ARAP3, ARMS2, batimastat, BCAM, BCAP31, BCAR1, benzyloxycarbonyl-Leu-Leu-Leu-aldehyde, BMP2, BMP4, BTC, C1QBP, $Ca^{2+}$, CA9, CADM1, CALR, calyculin A, caspase, CBL, CD209, CD36, CD44, CD46, CDH13, cerivastatin, chloramphenicol, chondroitin sulfate, CLEC4M, colchicine, Collagen type I, Collagen(s), COMP, CRK, CRP, CSF1, CSF2RB, CTGF, curcumin, CXCL12, cyclic AMP, DAB2, DAG1, DCN, DDR1, desferriexochelin 772SM, DOCK2, DSG2, DSG4, durapatite, Efna, EFNA1, EFNB, EFNB1, EGF, EGFR, EGR1, ELN, ENG, EP300, Eph Receptor, EPHA8, EPHB1, eptifibatide, ethylenediaminetetraacetic acid, ETS1, F11R, F3, FBLN5, FBN1, Fc receptor, FCN2, FERMT2, FES, FGF2, FGFR1, Fibrin, FN1, Focal adhesion kinase, FSH, FUT3, FUT6, FUT7, FYN, HACD1, heparin, Histone h3, Histone h4, HRAS, HSPG2, HTN1, hyaluronic acid, hydrocortisone, hydrogen peroxide, ICAM1, ICAM2, IGF1R, IgG, Igg3, IL1, IL1B, IL6, ILK, Integrin, Integrin alpha 4 beta 1, Integrinα, IPO9, ITGA1, ITGA2, ITGA3, ITGA5, ITGA6, ITGB1, ITGB2, ITGB3, ITGB5, JAK2, Jnk, KP-SD-1, LAMC1, Laminin, Laminin1, levothyroxine, LGALS3, LIF, lipopolysaccharide, LOX, LRP1, LRPAP1, MAD1L1, mannose, MAPK7, MBL2, MERTK, metronidazole, MGAT5, MMP2, Mn$^{2+}$, NCK, NEDD9, NRG1, okadaic acid, OLR1, P38 MAPK, PDGF BB, phosphatidylinositol, PKM, platelet activating factor, PLD1, PLG, PMP22, PODXL, POSTN, PRKCD, PTAFR, PTEN, PTGER2, PTK2, PTK2B, PTN, PTPN11, PTPRZ1, pyrrolidine dithiocarbamate, Rac, RALB, RANBP9, RHOA, RHOB, RPSA, SDC3, SELE, Selectin, SELL, SEMA3A, simvastatin, SIRPA, SPARC, sphingosine-1-phosphate, SPI1, SPP1, SPRY2, SRC, STARD13, SWAP70, TEK, TFPI, TFPI2, TGFA, TGFB1, TGFBI, TGM2, THBS2, THY1, thyroid hormone, TIMP2, tirofiban, TLN1, TLN2, TNF, TP63, tretinoin, VAV1, VCAM1, VCAN, Vegf, VHL, VTN, VWF, and WRR-086.

Of the 197 genes regulating cell attachment, 17 molecules were differentially expressed in the Schwann cell cultures, leading to an overall slightly increased attachment.

The results are relevant for an anti-scarring effect of dextran sulfate (see EXAMPLE 1) by reducing the signals of tissue fibrosis and adhesion of immune cells.

Upstream Regulator Pathways Affected by Dextran Sulfate

In Schwann cells, the upstream regulator analysis revealed that dextran sulfate modulated the effect of several growth factors by either increasing their activation or reducing their inhibition in the system as shown in Table 6.

containing leucine repeats with a glucosaminoglycan (GAG) chain consisting of either chondroitin sulfate or dermatan sulfate. It binds to type I collagen fibrils through the decorin type I collagen binding region.

Decorin acts as a transforming growth factor beta ½ (TGF-β½) antagonist and reduces scarring. Reports show that in acute scarring the dominant effect of decorin is anti-fibrogenic through suppression of inflammatory fibrosis by neutralization of TGF-β½. Decorin also binds directly to collagen and one of its functions is to influence on the organization of collagen during wound healing.

Decorin has previously been described in inhibition of scarring in a model of cerebral lesion, hydrocephalus, and chronic spinal cord wounds. Decorin also induces fibrolysis of existing trabecular meshwork scars in a glaucoma model.

Dextran sulfate induced an increase in decorin expression with a fold change of 1.242.

Conclusions

In Schwann cells, the control cultures, with high nutrient content and glucose, recapitulate the activation of Schwann cells. The dextran sulfate treated cultures mimicked the effect of dextran sulfate added after 24 hours of glial activation.

It is clear from the results that the molecular effects seen in Schwann cells support a role for dextran sulfate in

TABLE 6

Upstream regulator comparison in Schwann cells

| Analysis | Upstream regulator | Predicted activation state relative D2 control | Activation z-score | p-value of overlap |
|---|---|---|---|---|
| D2 control | ANGPT2 | | 1.062 | 0.003 |
| D2 dextran sulfate treatment | | Activated | 1.283 | 0.00373 |
| D2 control | BMP2 | | 0.674 | 0.0126 |
| D2 dextran sulfate treatment | | Activated | 1.395 | 0.00326 |
| D2 control | BMP4 | | −0.272 | 0.00253 |
| D2 dextran sulfate treatment | | Activated | 0.927 | 0.000663 |
| D2 control | BMP7 | | 1.45 | 0.0346 |
| D2 dextran sulfate treatment | | Activated | 1.86 | 0.0225 |
| D2 control | EGF | | −0.015 | 0.0000927 |
| D2 dextran sulfate treatment | | Activated | 2.059 | 0.00735 |
| D2 control | FGF2 | | 1.366 | 0.0000142 |
| D2 dextran sulfate treatment | | Activated | 2.37 | 0.000395 |
| D2 control | GDF2 | | 1.556 | 0.000299 |
| D2 dextran sulfate treatment | | Activated | 2.561 | 0.000106 |
| D2 control | HGF | | −0.823 | 0.0114 |
| D2 dextran sulfate treatment | | Activated | 1.432 | 0.0161 |
| D2 control | IGF1 | | 0.365 | 0.00883 |
| D2 dextran sulfate treatment | | Activated | 1.332 | 0.0132 |
| D2 control | NRG1 | | 1.073 | 0.0473 |
| D2 dextran sulfate treatment | | Activated | 1.768 | 0.143 |
| D2 control | NRTN | | | 0.0118 |
| D2 dextran sulfate treatment | | Activated | 0.958 | 0.0149 |
| D2 control | PGF | | 0 | 0.00185 |
| D2 dextran sulfate treatment | | Activated | 0.254 | 0.00871 |
| D2 control | TGFβ1 | | −1.239 | 0.0000354 |
| D2 dextran sulfate treatment | | Less inhibited | 1.05 | 0.0000691 |
| D2 control | VEGFA | | 1.909 | 0.00981 |
| D2 dextran sulfate treatment | | Activated | 3.4 | 0.00186 |
| D2 control | WISP2 | | −1.067 | 0.0323 |
| D2 dextran sulfate treatment | | Less inhibited | −0.896 | 0.0349 |

Dextran Sulfate Upregulate the Decorin Gene

Interestingly, the gene expression data showed that dextran sulfate activated the production of a natural scar reducing molecule called decorin, which further blocks scar production by 'mopping up' the growth factors that stimulate scar production by fibroblasts.

Decorin is a glycoprotein of on average 90-140 kD molecular weight. It belongs to the small-leucine rich proteoglycan (SLRP) family and consists of a protein core protection against apoptosis; induction of angiogenesis; increased migration and movement of cells; increased cell viability and survival; and induction of cellular differentiation.

Dextran sulfate promoted cell detachment and movement in Schwann cells. The effect on cell adhesion was mainly due to the expression of metalloproteinase-type enzymes, but the modulation of other adhesion molecules contributed to this effect as well.

This finding would also explain an anti-scarring effect of dextran sulfate as seen in EXAMPLE 1. The result suggests that the anti-scarring effect seen in EXAMPLE 1 is mediated by dextran sulfate activating degrading enzymes that help tissue remodeling and block the fibrogenic (scarring) signals in damaged tissues.

Scarring as a pathological reaction is driven by TGF-β. TGF-β induces a large interconnected network of 171 molecules causing adhesion of immune cells, activation of cells, cell movement, aggregation of cells, fibrosis and induction of TGF-β. Administration of dextran sulfate totally abolished the TGF-β-induced effect in adhesion of immune cells, activation of cells, aggregation of cells, fibrosis and self-activation of TGF-β. These inactivating effects of dextran sulfate on the molecular networks driven by TGF-β in Schwann cells are also seen even when TGF-β is activated, i.e., even in the presence of excessive TGF-β.

The analysis of the upstream regulators of the genes regulated by dextran sulfate indicated that dextran sulfate enhanced the effect of existing growth factors on cells, similar to the effect of heparin. A hypothesis is that dextran sulfate binds to the growth factor molecules and facilitates binding to their receptors.

The anti-scarring actions of dextran sulfate indicate a potential use to treat fibroproliferative (scarring) conditions, including glaucoma. The experimental results support the role of dextran sulfate in both preventing the development of fibroproliferative (scarring) conditions and resolving already established fibrotic scars in such fibroproliferative (scarring) conditions.

Thus, the dextran sulfate having an anti-scarring effect would be effective in tissue remodeling, in which there is a need for dissolving already established scars. This anti-scarring effect of dextran sulfate is thought to be a consequence of the previously described mechanisms of action of dextran sulfate including, for instance, inhibition of cell adhesion, induction of cell mobilization, induction of metalloproteases and scar dissolving enzymes, and inhibition of TGF-β, in particular TGF-β1, through the induction of decorin. This latter effect obtained with dextran sulfate is further of relevance in preventing or at least inhibiting fibrosis and scar formation through the induction of decorin.

Material and Methods
Experimental Design n=8×25 cm$^2$ culture flasks were set up. Two flasks were harvested on the day of treatment (24 hours after seeding). This represents the Day0 time point. From the remaining flasks, three flasks were treated with Control Medium and three were treated with Culture Medium (CM) containing dextran sulfate to give a final concentration of 0.01 mg/ml. Cells from the treated flasks were collected after 48 hours. Therefore the collected data represent (a) untreated cells (Day0 Controls and Day2 Controls) and (b) cells treated with dextran sulfate for 48 hours (Day2 dextran sulfate treated).

Coating of Tissue Culture Plates for All Cells 25 cm$^2$ flasks were coated by adding 2 ml per flask of a solution of 50 µg/ml poly-d-lysine in Hank's balanced salt solution (HBSS) and incubating overnight at 37° C. in the dark. Flasks were washed with cell culture water and air-dried for 30 min in the dark. Flasks were coated by adding 1 ml per flask of a solution of 25 µg/ml laminin in phosphate-buffered saline (PBS) and incubating for 2 hour at 37° C. in the dark. The laminin flasks were washed with PBS three times before plating cells.

Human Schwann Cells

Schwann cells growth medium was prepared by adding 10% of fetal bovine serum (FBS) to high-glucose DMEM and pre-warmed to 37° C. Cells were thawed in a 37° C. water bath for no longer than 2 min.

Cells from 12 vials were each gently transferred to a tube containing 10 ml of high-glucose DMEM medium and centrifuged at 400 relative centrifugal field (RCF) for 10 min. Pellet was resuspended in culture medium. The cells from the 12 vials were mixed and distributed equally into the previously coated 25 cm$^2$ flasks (n=8). Cells were incubated at 37° C. with 5% $CO_2$. Cells were allowed to settle for 24 hours before dextran sulfate treatment.

Drug Treatment

Dextran sulfate (Tikomed AB, Sweden, WO 2016/076780) was provided at a stock concentration of 20 mg/ml and was kept in a temperature monitored refrigerator at 4° C. A fresh 100× dextran sulfate stock (1.0 mg/ml) was prepared in sterile DMEM-F12. The concentrated drug stock was sterile filtered and added to the respective culture media (19.6 ml CM and 0.4 ml dextran sulfate stock solution). The Control was made using 19.6 ml CM and 0.4 ml of DMEM-F12. Dextran sulfate and CM were added to the respective flasks (5 ml each) to reach the 0.01 mg/ml concentration of dextran sulfate in each dish with a total of 10 ml CM each.

Culture Collection and Cell Lysis.

CM was aspirated into a clean and labelled 15 ml Falcon tube. The flasks (without culture medium) were placed into the −80° C. freezer for 30 minutes. The CM in the Falcon tubes were spun at 3000×g for 5 minutes. Supernatant was removed and the small pellet was re-suspended in 2.5 ml Trizol:Water (4:1) solution at room temperature (RT, ~22° C.).

The frozen flasks were removed one-by one from the freezer and the Trizol-Water from the appropriate tubes was moved to the flask. Flasks were left at RT for 5 minutes before the content was aspirated back into the 15 ml Falcon tube (after washing the bottom of the flask with the solution thoroughly). The flasks were inspected under the microscope to ensure full removal of cells. The collected lysates in the 15 ml Falcon tubes were placed into the −80° C. freezer.

RNA Extraction

Falcon tubes containing the homogenates were removed from the freezer and stored for 5 minutes at RT to permit the complete dissociation of nucleoprotein complexes.

Two aliquots of 1 ml lysate was removed from each sample and 200 µl of chloroform was added to each (0.2 ml of chloroform per 1 ml of TRIzol Reagent used during the cell lysis step) and the tube was shaken vigorously. Samples were stored at RT for 2-3 minutes and subsequently centrifuged at 12,000×g for 15 minutes at 4° C.

The mixture separated into three layers: a lower red phenol-chloroform phase, an interphase and a colorless upper aqueous phase. The RNA remained in the top aqueous phase, DNA in the white middle (interphase) phase and protein in the pink bottom (organic) phase. The top ¾ of the aqueous phase was transferred to a new clean Eppendorf tube.

The RNA was precipitated from the aqueous phase by adding an equal amount of 100% ethanol. The precipitated RNA was fixed onto a Spin Cartridge, washed twice and dried. The RNA was eluted in 50 µl warm RNase-Free Water. The amount and quality of the purified RNA was measured by Nanodrop. The RNA was stored at −80° C. before transfer to Source Bioscience for Array analysis.

Analysis Plan for Expression Data

The expression data were downloaded into separate files for each cell line. The 'Background corrected' expression is the data from the "gProcessedSignal" of the arrays that is the result of the background signal extracted from the actual signal of the relevant probe. This is the most often used variable in array analysis. The background corrected signal was log 2 transformed for all samples for statistical analysis. To reduce the false discovery rate in the samples, the signals that were below 'expression level' were removed. The 'below expression' level was set at 5 for the log 2 transformed expression values.

Statistical Analysis

Based on the expression pattern of the Control probes on each array it was decided to carry out Median Centering for all arrays before analysis to reduce the variability of the results. Data was analyzed using the following algorithms:

Comparison of D0 control to D2 control samples—expression changes seen in the cells in normal cultures Comparison of D0 control to D2 dextran sulfate treated samples—expression changes seen in the cells in the dextran sulfate treated cultures Comparison of D2 control to D2 dextran sulfate treated samples—differential expression induced by dextran sulfate in the culture.

A preliminary analysis was carried out to screen out genes that were not differentially expressed between any combination of the three datasets. Simple, non-stringent ANOVA ($p<0.05$) was carried out to look for patterns of expression. Probes with no changes across the three datasets were eliminated. The remaining probe sets were analyzed for fold change and significance using Volcano plots. More than 20% change in the expression of a probe (FC≥1.2 or FC≤0.84) was regarded as significant in the first instance to allow the detection of expression patterns.

Quality Parameters

Seeding densities were calculated from the cell counts retrieved from the cell stocks for the Schwann cells.

The additional quality control from the Array service provider indicated that the RNA was high quality (no degradation) and the amounts were within the parameters of the Low input RNA microarray from Agilent.

The analysis of the raw data indicated that, as expected, there were significant differences between arrays. These differences (reflected by differences in the same control samples included on all arrays), were, however, easily eliminated by normalization techniques. The chosen median centering of the data that eliminates the array-to-array variation did not affect the overall differences expected to be seen between the controls representing different concentrations of RNA.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

[1] Hill et al., Decorin reduces intraocular pressure and retinal ganglion cell loss in rodents through fibrolysis of the scarred trabecular meshwork. *Invest Ophthalmol Vis Sci*. 2015, 56(6): 3743-3757

[2] Chen et al., RAGE regulates immune cell infiltration and angiogenesis in choroidal neovascularization. *Plos One*. 2014, 9(2): e89548

[3] Chen et al., Age- and light-dependent development of localised retinal atrophy in CCL2 (−/−) CX3CR1 (GFP/GFP) mice. *Plos One*. 2013, 8(4): e61381

The invention claimed is:

1. A method for treating glaucoma in a subject suffering from glaucoma, said method comprising administering dextran sulfate, or a pharmaceutically acceptable salt thereof, having an average molecular weight equal to or below 10,000 Da to said subject suffering from glaucoma.

2. The method according to claim 1, wherein said subject is suffering from open-angle glaucoma.

3. The method according to claim 1, wherein said subject is suffering from primary open-angle glaucoma in said subject.

4. The method according to claim 1, wherein administering dextran sulfate, or a pharmaceutically acceptable salt thereof, comprises systemically administering dextran sulfate, or a pharmaceutically acceptable salt thereof, to said subject.

5. The method according to claim 4, wherein systemically administering dextran sulfate, or a pharmaceutically acceptable salt thereof, comprises intravenously administering dextran sulfate, or a pharmaceutically acceptable salt thereof, to said subject.

6. The method according to claim 4, wherein systemically administering dextran sulfate, or a pharmaceutically acceptable salt thereof, comprises subcutaneously administering dextran sulfate, or a pharmaceutically acceptable salt thereof, to said subject.

7. The method according to claim 1, wherein said average molecular weight is within a range of 2000 and 10,000 Da.

8. The method according to claim 7, wherein said average molecular weight is within a range of 3000 and 10,000 Da.

9. The method according to claim 8, wherein said average molecular weight is within a range of 3500 and 9500 Da.

10. The method according to claim 9, wherein said average molecular weight is within a range of 4500 and 7500 Da.

11. The method according to claim 10, wherein said average molecular weight is within a range of 4500 and 5500 Da.

12. The method according to claim 1, wherein said dextran sulfate, or said pharmaceutically acceptable salt thereof, has an average sulfur content in a range from 15 to 20%.

13. The method according to claim 12, wherein said dextran sulfate, or said pharmaceutically acceptable salt thereof, has an average sulfur content of about 17%.

14. The method according to claim 1, wherein said dextran sulfate, or said pharmaceutically acceptable salt thereof, has a number average molecular weight ($M_n$) as measured by nuclear magnetic resonance (NMR) spectroscopy within an interval of 1850 and 3500 Da.

15. The method according to claim 14, wherein said dextran sulfate, or said pharmaceutically acceptable salt thereof, has a $M_n$ as measured by NMR spectroscopy within an interval of 1850 and 2500 Da.

16. The method according to claim 15, wherein said dextran sulfate, or said pharmaceutically acceptable salt thereof, has a $M_n$ as measured by NMR spectroscopy within an interval of 1850 and 2300 Da.

17. The method according to claim 16, wherein said dextran sulfate, or said pharmaceutically acceptable salt thereof, has a $M_n$ as measured by NMR spectroscopy within an interval of 1850 and 2000 Da.

18. The method according to claim 14, wherein said dextran sulfate, or said pharmaceutically acceptable salt thereof, has an average sulfate number per glucose unit within an interval of 2.5 and 3.0.

19. The method according to claim 18, wherein said dextran sulfate, or said pharmaceutically acceptable salt thereof, has an average sulfate number per glucose unit within an interval of 2.5 and 2.8.

20. The method according to claim 19, wherein said dextran sulfate, or said pharmaceutically acceptable salt thereof, has an average sulfate number per glucose unit within an interval of 2.6 and 2.7.

21. The method according to claim 1, wherein said dextran sulfate, or said pharmaceutically acceptable salt thereof, has on average 5.1 glucose units and an average sulfate number per glucose unit of 2.6 to 2.7.

22. The method according to claim 1, wherein said dextran sulfate, or said pharmaceutically acceptable salt thereof, is formulated as an aqueous injection solution.

23. The method according to claim 1, wherein said pharmaceutically acceptable salt thereof is a sodium salt of dextran sulfate.

24. A method for reducing intraocular pressure in a subject suffering from glaucoma, said method comprising administering dextran sulfate, or said pharmaceutically acceptable salt thereof, having an average molecular weight equal to or below 10,000 Da to said subject.

25. The method according to claim 24, wherein administering dextran sulfate, or said pharmaceutically acceptable salt thereof, comprises administering dextran sulfate, or said pharmaceutically acceptable salt thereof, to said subject to reduce intraocular pressure to be within a normal intraocular pressure range from 10 mmHg up to 20 mmHg.

26. A method for treating ocular hypertension in a subject suffering from ocular hypertension, said method comprising administering dextran sulfate, or a pharmaceutically acceptable salt thereof, having an average molecular weight equal to or below 10,000 Da to the subject suffering from ocular hypertension.

27. A method for inhibiting loss of retinal ganglion cells and reduction of retinal nerve fiber layer in a subject suffering from at least one of glaucoma and ocular hypertension, said method comprising administering dextran sulfate, or a pharmaceutically acceptable salt thereof, having an average molecular weight equal to or below 10,000 Da to said subject.

* * * * *